US008946432B2

(12) United States Patent
Sinha et al.

(10) Patent No.: US 8,946,432 B2
(45) Date of Patent: Feb. 3, 2015

(54) BIARYL DERIVATIVES AS NACHR MODULATORS

(75) Inventors: Neelima Sinha, Maharashtra (IN); Navnath Popat Karche, Maharashtra (IN); Girish Dhanraj Hatnapure, Maharashtra (IN); Anil Kashiram Hajare, Maharashtra (IN); Venkata P. Palle, Maharashtra (IN); Rajender Kumar Kamboj, Maharashtra (IN)

(73) Assignee: Lupin Limited, Mumbai, Maharashtra (IN)

( * ) Notice: Subject to any disclaimer, the term of this patent is extended or adjusted under 35 U.S.C. 154(b) by 0 days.

(21) Appl. No.: 14/130,815

(22) PCT Filed: Jul. 2, 2012

(86) PCT No.: PCT/IB2012/053347
§ 371 (c)(1),
(2), (4) Date: Jan. 3, 2014

(87) PCT Pub. No.: WO2013/005153
PCT Pub. Date: Jan. 10, 2013

(65) Prior Publication Data
US 2014/0155433 A1 Jun. 5, 2014

(30) Foreign Application Priority Data
Jul. 5, 2011 (IN) .............................. 906/KOL/2011

(51) Int. Cl.
C07D 207/335 (2006.01)
C07D 277/28 (2006.01)
C07D 333/22 (2006.01)
C07D 417/12 (2006.01)
C07D 277/56 (2006.01)
A61K 31/381 (2006.01)
A61K 31/401 (2006.01)
A61K 31/4025 (2006.01)
A61K 31/426 (2006.01)
C07D 277/30 (2006.01)
A61K 45/06 (2006.01)
A61K 31/4164 (2006.01)
A61K 31/40 (2006.01)
A61K 31/427 (2006.01)
A61K 31/454 (2006.01)

(52) U.S. Cl.
CPC ............ *C07D 277/56* (2013.01); *A61K 31/381* (2013.01); *A61K 31/401* (2013.01); *A61K 31/4025* (2013.01); *A61K 31/426* (2013.01); *C07D 207/335* (2013.01); *C07D 277/28* (2013.01); *C07D 277/30* (2013.01); *C07D 333/22* (2013.01); *A61K 45/06* (2013.01); *A61K 31/4164* (2013.01); *A61K 31/40* (2013.01); *A61K 31/427* (2013.01); *A61K 31/454* (2013.01); *C07D 417/12* (2013.01)

USPC ............. 546/209; 548/200; 548/540; 549/72

(58) Field of Classification Search
None
See application file for complete search history.

(56) References Cited

U.S. PATENT DOCUMENTS

| 4,235,871 A | 11/1980 | Papahadjopoulos et al. |
| 4,501,728 A | 2/1985 | Geho et al. |
| 4,837,028 A | 6/1989 | Allen |
| 5,019,369 A | 5/1991 | Presant et al. |
| 5,608,082 A | 3/1997 | Varney et al. |
| 5,668,161 A | 9/1997 | Talley et al. |
| 7,683,084 B2 | 3/2010 | Faghih et al. |
| 7,741,364 B2 | 6/2010 | Faghih et al. |
| 2006/0142349 A1 | 6/2006 | Hurst et al. |
| 2007/0142450 A1 | 6/2007 | Dahl et al. |
| 2009/0018104 A1* | 1/2009 | Sato et al. ........................ 514/64 |
| 2009/0253691 A1 | 10/2009 | Thuring et al. |
| 2010/0190819 A1 | 7/2010 | Kanner |
| 2010/0222398 A1 | 9/2010 | Nardi et al. |
| 2010/0227869 A1 | 9/2010 | Peters et al. |
| 2010/0240707 A1 | 9/2010 | Thuring et al. |

FOREIGN PATENT DOCUMENTS

| EP | 1 012 142 | 3/1999 |
| EP | 1 866 314 | 8/2006 |
| EP | 1 932 832 | 6/2008 |

(Continued)

OTHER PUBLICATIONS

Albuquerque et al., "Modulation of Nicotinic Receptor Activity in the Central Nervous System: A Novel Approach to the Treatment of Alzheimer Disease", *Alzheimer Disease and Associated Disorders*, vol. 15, Suppl. 1, 2001, pp. S19-S25.

(Continued)

*Primary Examiner* — Janet L Andres
*Assistant Examiner* — Timothy R Rozof
(74) *Attorney, Agent, or Firm* — Merchant & Gould P.C.

(57) ABSTRACT

Disclosed is a compound of formula (I): wherein 'D', 'E', 'm', 'n' and $R^1$-$R^4$ are as described herein, as a modulator of nicotinic acetylcholine receptors particularly the α7 subtype, in a subject in need thereof, as well as analogues, prodrugs, isotopically substituted analogs, metabolites, pharmaceutically acceptable salts, polymorphs, solvates, isomers, clathrates, and co-crystal thereof, for use either alone or in combinations with suitable other medicaments, and pharmaceutical compositions containing such compounds and analogues. Also disclosed are a process of preparation of the compounds and the intended uses thereof in therapy, particularly in the prophylaxis and therapy of disorders such as Alzheimer's disease, mild cognitive impairment, senile dementia, and the like.

10 Claims, No Drawings

(56) References Cited

FOREIGN PATENT DOCUMENTS

| EP | 1 992 361 | 11/2008 |
|---|---|---|
| WO | WO 99/14194 | 3/1999 |
| WO | WO 02/15662 | 2/2002 |
| WO | WO 02/16355 | 2/2002 |
| WO | WO 02/17358 | 2/2002 |
| WO | WO 03/018585 | 3/2003 |
| WO | WO 2005/042540 | 5/2005 |
| WO | WO 2006/087305 | 8/2006 |
| WO | WO 2006/089076 | 8/2006 |
| WO | WO 2006/092056 | 9/2006 |
| WO | WO 2007/031440 | 3/2007 |
| WO | WO 2007/092751 | 8/2007 |
| WO | WO 2007/125934 | 11/2007 |
| WO | WO 2008/036541 | 3/2008 |
| WO | WO 2009/043780 | 4/2009 |
| WO | WO 2009/043784 | 4/2009 |
| WO | WO 2009/115547 | 9/2009 |
| WO | WO 2009/127678 | 10/2009 |
| WO | WO 2009/127679 | 10/2009 |
| WO | WO 2009/135944 | 11/2009 |
| WO | WO 2009/145996 | 12/2009 |
| WO | WO 2010/130768 | 11/2010 |
| WO | WO 2011/036167 | 3/2011 |
| WO | WO 2011/064288 | 6/2011 |

OTHER PUBLICATIONS

Alkondon et al., "α7 Nicotinic acetylcholine receptors and modulation of gabaergic synaptic transmission in the hippocampus", *European Journal of Pharmacology*, vol. 393, 2000, pp. 59-67.

Arias et al., "Role of non-neuronal nicotinic acetylcholine receptors in angiogenesis", *The International Journal of Biochemistry & Cell Biology*, vol. 41, 2009, pp. 1441-1451.

Bennouna et al., "Cholinergic hypothesis in psychosis following traumatic brain injury and cholinergic hypothesis in schizophrenia: a link?", *L'Encéphale*, vol. 33, No. 1, 2007, pp. 616-620.

Berge et al., "Pharmaceutical Salts", *Pharmaceutical Sciences*, vol. 66, No. 1, 1977, pp. 1-19.

Bitner et al., "Broad-Spectrum Efficacy across Cognitive Domains by α7 Nicotinic Acetylcholine Receptor Agonism Correlates with Activation of ERK1/2 and CREB Phosphorylation Pathways", *The Journal of Neuroscience*, vol. 27, No. 39, 2007, pp. 10578-10587.

Boess et al., "The Novel α7 Nicotinic Acetylcholine Receptor Agonist N-[(3R)-1-Azabicyclo[2.2.2]oct-3-yl]-7-[2-(methoxy)phenyl]-1-benzofuran-2-carboxamide Improves Working and Recognition Memory in Rodents", *The Journal of Pharmacology and Experimental Therapeutics*, vol. 321, No. 2, 2007, pp. 716-725.

Bruchfeld et al., "Whole blood cytokine attenuation by cholinergic agonists ex vivo and relationship to vague nerve activity in rheumatoid arthritis", *Journal of Internal Medicine*, vol. 268, 2010, pp. 94-101.

Calleja-Macias et al., "Cholinergic signaling through nicotinic acetylcholine receptors stimulates the proliferation of cervical cancer cells: An explanation for the molecular role of tobacco smoking in cervical carcinogenesis?", *Int. J. Cancer*, vol. 124, 2009, pp. 1090-1096.

Cannon, Tyrone D., "The inheritance of intermediate phenotypes for schizophrenia", *Current Opinion in Psychiatry*, vol. 18, 2005, pp. 135-140.

Carson et al., "Genetic Variation in the α7 Nicotinic Acetylcholine Receptor is Associated with Delusional Symptoms in Alzheimer's Disease", *Neuromol Med*, vol. 10, 2008, pp. 377-384.

Chan et al., "Frontal cortical α7 and α4β2 nicotinic acetylcholine receptors in working and reference memory", *Neuropharmacology*, vol. 52, 2007, pp. 1641-1649.

Chen et al., "A Cascade Approach to Pyridines from 2-Azido-2,4-dienoates and α-Diazocarbonyl Compounds", *J. Org. Chem*, vol. 74, 2009, pp. 903-905.

Curzon et al., "Antisense knockdown of the rat α7 nicotinic acetylcholine receptor produces spatial memory impairment", *Neuroscience Letters*, vol. 410, 2006, pp. 15-19.

Dajas-Bailador, "Nicotinic acetylcholine receptors and the regulation of neuronal signaling", *TRENDS in Pharmacological Sciences*, vol. 25, No. 6, 2004, pp. 317-324.

Damaj et al., "The antinociceptive effects of α7 nicotinic agonists in an acute pain model", *Neuropharmacology*, vol. 39, 2000, pp. 2785-2791.

Decker et al., "The therapeutic potential of nicotinic acetylcholine receptor agonists for pain control", *Expert Opin. Investig. Drugs*, vol. 10, No. 10, 2001, pp. 1819-1830.

Deutsch et al., "Progressive Worsening of Adaptive Functions in Down Syndrome May Be Mediated by the Complexing of Soluble Aβ Peptides With the $α_7$ Nicotinic Acetylcholine Receptor: Therapeutic Implications", *Clinical Neuropharmacology*, vol. 26, No. 5, 2003, pp. 227-283.

Dong et al., "Transition Metal-Catalyzed Synthesis of Pyrroles from Dienyl Azides", *Organic Letters*, vol. 9, No. 25, 2007, pp. 5191-5194.

Donnelly-Roberts, "ABT-594 [(R)-5-(2-Azetidinylmethoxy)-2-Chloropyridine]: A Novel, Orally Effective Analgesic Acting via Neuronal Nicotinic Acetylcholine Receptors: 1. In Vitro Characterization", *The Journal of Pharmacology and Experimental Therapeutics*, vol. 285, No. 2, 1998, pp. 777-786.

Dunlop et al., "Old and New Pharmacology: Positive Allosteric Modulation of the α7 Nicotinic Acetylcholine Receptor by the 5-Hydroxytryptamine$_{2B/C}$ Receptor Antagonist SB-206553 (3,5-Dihydro-5-methyl-N-3-pyridinylbenzo[1,2-b:4,5-b']di pyrrole-1(2H)-carboxamide)", *The Journal of Pharmacology and Experimental Therapeutics*, vol. 328, No. 3, pp. 766-776, (Mar. 2009).

Duris et al., "α7 Nicotinic Acetylcholine Receptor Agonist PNU-282987 Attenuates Early Brain Injury in a Perforation Model of Subarachnoid Hemorrhage in Rats", *Stroke*, vol. 42, 2011, pp. 3530-3536.

Ebbert et al., "Varenicline for smoking cessation: efficacy, safety, and treatment recommendations", *Patient Preference and Adherence*, vol. 4, 2010, pp. 355-362.

EnVivo Pharmaceuticals Press Release, "EnVivo Reports Positive Results of Its EVP-6124 Clinical Bio-Marker Study in Schizophrenia Patients", Jan. 12, 2009.

Faghih et al., "Discovery of 4-(5-(4-Chlorophenyl)-2-methyl-3-propionyl-1H-pyrrol-1-yl)benzenesulfonamide (A-86744) as a Novel Positive Allosteric Modulator of the α7 Nicotinic Acetylcholine Receptor", *J. Med. Chem*, vol. 52, 2009, pp. 3377-3384.

Fehér et al., "Association between a Genetic Variant of the Alpha-7 Nicotinic Acetylcholine Receptor Subunit and Four Types of Dementia", *Dement Geriatr Cogn Disord*, vol. 28, 2009, pp. 56-62.

Freedman et al., "Evidence in Postmortem Brain Tissue for Decreased Numbers of Hippocampal Nicotinic Receptors in Schizophrenia", *Biol Psychiatry*, vol. 38, 1995, pp. 22-33.

Freedman et al., "The Genetics of Sensory Gating Deficits in Schizophrenia", *Current Psychiatry Reports*, vol. 5, 2003, pp. 155-161.

Gallowitsch-Puerta et al., "Neuro-immune interactions via the cholinergic anti-inflammatory pathway", *Life Sci.*, vol. 80, No. 24-25, 2007, pp. 2325-2329.

Giebelen et al., "Stimulation of α7 Cholinergic Receptors Inhibits Lipopolysaccharide-Induced Neutrophil Recruitment by a Tumor Necrosis Factor α-Independent Mechanism", *Shock*, vol. 27, No. 4, 2007, pp. 443-447.

Goldstein et al., "Cholinergic Agonists Inhibit LPS Induced Whole Blood TNF Release Ex Vivo in Patients With Severe Sepsis: A Pilot Study", *Acad. Emerg. Med.*, vol. 14, No. 15, Suppl. 1, Abst 474, 2007, SAEM Annual Meeting Abstracts, pp. S7, S185-S-S186.

Greene et al., *Protective Groups in Organic Synthesis*, $3^{rd}$ ed., John Wiley & Sons, Inc.: 1999. (In 3 Parts).

Harrington et al., "Senile Dementia of Lewy Body Type and Alzheimer Type Are Biochemically Distinct in Terms of Paired Helical Filaments and Hyperphosphorylated Tau Protein", *Dementia*, vol. 5, 1994, pp. 215-228.

Hashimoto et al., "Phencyclidine-Induced Cognitive Deficits in Mice Are Improved by Subsequent Subchronic Administration of the Novel Selective α7 Nicotinic Receptor Agonist SSR180711", *Biol Psychiatry*, vol. 63, 2008, pp. 92-97.

(56) References Cited

OTHER PUBLICATIONS

Hauser et al., "An alpha7 neuronal nicotinic receptor-selective agonist that demonstrates efficacy in animal models of the positive and negative symptoms and cognitive dysfunction of schizophrenia", *Biochemical Pharmacology*, vol. 78, 2009, pp. 803-812.
Haydar et al., "SAR and biological evaluation of SEN12333/WAY-317538: Novel alpha 7 nicotinic acetylcholine receptor agonist", *Bioorganic & Medicinal Chemistry*, vol. 17, 2009, pp. 5247-5258.
Heeschen et al., "A novel angiogenic pathway mediated by non-neuronal nicotinic acetylcholine receptors", *The Journal of Clinical Investigation*, vol. 110, No. 4, 2002, pp. 527-536.
International Search Report and Written Opinion from International Application No. PCT/IB2012/053347 mailed Sep. 21, 2012.
Jeyarasasingam et al., "Stimulation of Non-α7 Nicotinic Receptors Partially Protects Dopaminergic Neurons From 1-Methyl-4-Phenylpyridinium-Induced Toxicity in Culture", *Neuroscience*, vol. 109, No. 2, 2002, pp. 275-285.
Jin et al., "Genomic polymorphisms within alpha 7 nicotinic acetylcholine receptor and severe sepsis in Chinese Han population", *International Journal of Immunogenetics*, vol. 37, 2010, pp. 361-365.
Kuzmin et al., "Effects of Subunit selective nACh receptors on operant ethanol self-administration and relapse-like ethanol-drinking behavior", *Psychopharmacology*, vol. 203, 2009, pp. 99-108.
Leiser et al., "A cog in cognition: How the α7 nicotinic acetylcholine receptor is geared towards improving cognitive deficits", *Pharmacology & Therapeutics*, vol. 122, Issue 3, 2009, pp. 302-311.
Leonard et al., "Smoking and mental illness", *Pharmacology, Biochemistry and Behavior*, vol. 70, 2001, pp. 561-570.
Liu et al., "Antishock effect of anisodamine involves a novel pathway for activating α7 nicotinic acetylcholine receptor", *Crit Care Med*, vol. 37, No. 2, 2009, pp. 634-641.
Mansvelder et al., "Nicotinic modulation of neuronal networks: from receptors to cognition", *Psychopharmacology*, vol. 184, 2006, pp. 292-305.
Marrero et al., "Convergence of alpha 7 nicotinic acetylcholine receptor-activated pathways for anti-apoptosis and anti-inflammation: Central role for JAK2 activation of STAT3 and NF-κB", *Brain Research*, vol. 1256, 2009, pp. 1-7.
Martin et al., "Alpha-7 nicotinic receptor agonists: potential new candidates for the treatment of schizophrenia", *Psychopharmacology*, vol. 174, 2004, pp. 54-64.
Martin et al., "Sensory Gating and Alpha-7 Nicotinic Receptor Gene Allelic Variants in Schizoaffective Disorder, Biopolar Type", *Americal Journal of Medical Genetics Park B (Neuropsychiatric Genetics)*, vol. 144B, 2007, pp. 611-614.
McKay et al., "Regulation of synaptic transmission and plasticity by neuronal nicotinic acetylcholine receptors", Biochemical Pharmacology, vol. 74, 2007, pp. 1120-1133.
Miyaura et al., "Palladium-Catalyzed Cross-Coupling Reactions of Organoboron Compounds", *Chem. Rev.*, vol. 95, 1995, pp. 2457-2483.
Nagele et al., "Intracellular Accumulation of β-Amyloid$_{1-42}$ in Neurons is Facilitated by the α7 Nicotinic Acetylcholine Receptor in Alzheimer's Disease", *Neuroscience*, vol. 110, No. 2, 2002, pp. 199-211.
Ng et al., "Nootropic α7 nicotinic receptor allosteric modulator derviced from GABA$_A$ receptor modulators", *PNAS*, vol. 104, No. 19, 2007, pp. 8059-8064.
Nizri et al., "The Role of Cholinergic Balance Perturbation in Neurological Diseases", *Drug News Perspect*, vol. 20, No. 7, 2007, pp. 421-429.
Nordberg, Agneta, "Neuroprotection in Alzheimer's Disease—New Strategies for Treatment", *Neurotoxicity Research*, vol. 2, 2000, pp. 157-165.
O'Donnell et al., "Discovery of 4-(5-Methyloxazolo[4,5-*b*]pyridine-2-yl)-1,4-diazabicyclo[3.2.2]nonane (CP-810,123), a Novel α7 Nicotinic Acetylcholine Receptor Agonist for the Treatment of Cognitive Disorders in Schizophrenia: Synthesis, SAR Development, and in Vivo Efficacy in Cognition Models", *J. Med. Chem.*, vol. 53, 2010, pp. 1222-1237.
Olincy, Aim, "Nicotine Receptor Dysfunction in Schizophrenia and Therapeutic Effects of Nicotine Agonist DMXBA", *Biol Psychiatry*, vol. 57, Abstract 44, 2005, 1S-212S.
Olincy et al., "Proof-of-Concept Trial of an α7 Nicotinic Agonist in Schizophrenia", *Arch Gen Psychiatry*, vol. 63, 2006, pp. 630-638.
Paterson et al., "Neuronal nicotinic receptors in the human brain", *Progress in Neurobiology*, vol. 61, 2000, pp. 75-111.
Peña et al., "Unphosphorylated STAT3 modulates alpha7 nicotinic receptor signaling and cytokine production in sepsis", *European Journal of Immunology*, vol. 40, 2010, pp. 2580-2589.
Peng et al., "The transmission disequilibrium analysis between neuronal nicotinic acetylcholine receptor α7 subunit gene polymorphisms and schizophrenia", *Chin J Med Genet.*, vol. 25, No. 2, 2008, pp. 154-158.
Perry et al., "Nicotinic receptor subtypes in human brain ageing, Alzheimer and Lewy body diseases", *European Journal of Pharmacology*, vol. 393, 2000, pp. 215-222.
*Physicians' Desk Reference*, 58$^{th}$ Ed., Thomson PDR, 2004, pp. 303-340, 1221-1223, 1759-1764, 2252-2259, 2570-2573.
Pichat et al., "SSRI807I I, a Novel Selective α7 Nicotinic Receptor Partial Agonist: (II) Efficacy in Experimental Models Predictive of Activity Against Cognitive Symptoms of Schizophrenia", *Neuropsychopharmacology*, vol. 32, 2007, pp. 17-34.
Redrobe et al., "α7 nicotinic acetylcholine receptor activation ameliorates scopolamine-induced behavioural changes in a modified continuour Y-maze task in mice", *European Journal of Pharmacology*, vol. 602, 2009, pp. 58-65.
*Remington's Pharmaceutical Sciences*, 17$^{th}$ ed., Mack Publishing Company: Easton, PA, 1985, pp. 1518-1552.
*Remington's Pharmaceutical Sciences*, 18$^{th}$ ed., Mack Publishing Company: Easton, PA, 1985, p. 1445.
Roncrati et al., "Procognitive and Neuroprotective Activity of a Novel α7 Nicotinic Acetylcholine Receptor Agonist for Treatment of Neurodegenerative and Cognitive Disorders", *The Journal of Pharmacology and Experimental Therapeutics*, vol. 329, No. 2, 2009, pp. 459-468.
Rosas-Ballina et al., "Cholinergic control of inflammation", *Journal of Internal Medicine*, vol. 265, 2009, pp. 663-679.
Rosas-Ballina et al., "The Selective α7 Agonist GTS-21 Attenuates Cytokine Production in Human Whole Blood and Human Monocytes Activated by Ligands for TLR2, TLR3, TLR4, TLR9, and RAGE", *Mol Med*, vol. 15, No. 7-8, 2009, pp. 195-202.
Rowbotham et al., "A randomized, double-blind, placebo-controlled trial evaluating the efficacy and safety of ABT-594 in patients with diabetic peripheral neuropathic pain", *PAIN*, vol. 146, 2009, pp. 245-252.
Rowley et al., "Antinoceptive and anti-inflammatory effects of choline in a mouse model of postoperative pain", *British Journal of Anaesthesia*, vol. 105, No. 2, 2010, pp. 201-207.
Rubboli et al., "Distribution of Neuronal Nicotinic Receptor Subunits in Human Brain", *Neurochem. Int.*, vol. 25, No. 1, 1994, pp. 69-71.
Sanberg et al., "Nicotine for the Treatment of Tourette's Syndrome", *Pharmacol. Ther.*, vol. 74, No. 1, 1997, pp. 21-25.
Schuller et al., "Interaction of tobacco-specific toxicants with the neuronal α$_7$ nicotinic acetylcholine receptor and its associated mitogenic signal transduction pathway: potential role in lung carcinogenesis and pediatric lung disorders", *European Journal of Pharmacology*, vol. 393, 2000, pp. 265-277.
Silva et al., "A Simple Preparation of N,N-Dimethyl-N'-Alkyl (Aryl) Sulfonylformamidines", *Organic Preparations and Procedures International*, vol. 34. No. 5, 2002, pp. 545-549.
Solinas et al., "Nicotinic α$_7$ Receptors as a New Target for Treatment of Cannabis Abuse", *The Journal of Neuroscience*, vol. 27, No. 21, 2007, pp. 5615-5620.
Stahl et al., *Handbook of Pharmaceutical Salts Properties, Selection, and Use*, Wiley-VCH: Zürich, Switzerland, 2002.
Suemaru et al., "Involvement of neuronal nicotinic receptor in psychiatric disorders", *Folia Pharmacol. Jpn.*, vol. 119, 2002, pp. 295-300 (Abstract in English).
Sydnes et al., "Reductive monoalkylation of nitro aryls in one-pot", *Tetrahedron*, vol. 64, 2008, pp. 6406-6414.

(56) References Cited

OTHER PUBLICATIONS

Szoka et al., "Comparative Properties and Methods of Preparation of Lipid Vesicles (Liposomes)", *Ann. Rev. Biophys. Bioeng.*, vol. 9, 1980, pp. 467-508.

Thomsen et al., "Cognitive Improvement by Activation of $\alpha_7$ Nicotinic Acetylcholine Receptors: From Animal Models to Human Pathophysiology", *Current Pharmaceutical Design*, vol. 16, 2010, pp. 323-343.

Timmermann et al., "An Allosteric Modulator of the $\alpha 7$ Nicotinic Acetylcholine Receptor Possessing Cognition-Enhancing Properties in Vivo", *The Journal of Pharmacology and Experimental Therapeutics*, vol. 323, No. 1, 2007, pp. 294-307.

Tsuang et al., "Examination of Genetic Linkage of Chromosome 15 to Schizophrenia in a Large Veterans Affairs Cooperative Study Sample", *American Journal of Medical Genetics (Neuropsychiatric Genetics)*, vol. 105, 2001, pp. 662-668.

van Kampen et al., "AR-R 17779 improves social recognition in rats by activation of nicotinic $\alpha 7$ receptors", *Psychopharmacology*, vol. 172, 2004, pp. 375-383.

Verbois et al., "Chronic nicotine treatment attenuates $\alpha 7$ nicotinic receptor deficits following traumatic brain injury", *Neuropharmacology*, vol. 44, 2003, pp. 224-233.

Wang et al., "Dissociating $\beta$-Amyloid from $\alpha 7$ Nicotinic Acetylcholine Receptor by a Novel Therapeutic Agent, S 24795, Normalizes $\alpha 7$ Nicotinic Acetylcholine and NMDA Receptor Function in Alzheimer's Disease Brain", *The Journal of Neuroscience*, vol. 29, No. 35, 2009, pp. 10961-10973.

Wang et al., "Huperzine A Improves Chronic Inflammation and Cognitive Decline in Rats With Cerebral Hypoperfusion", *Journal of Neuroscience Research*, vol. 88, 2010, pp. 807-815.

Wasserman et al., "Clinical Comparison of The Nitrosoureas", *Cancer*, vol. 36, No. 4, 1975, pp. 1258-1268.

Weiss et al., "A Candidate Gene Approach Identifies the *CHRNA5-A3-B4* Region as a Risk Factor for Age-Dependent Nicotine Addiction", *PLOS Genetics*, vol. 4, Issue 7, 2008, pp. 1-11

Westman et al., "Cell Specific Synovial Expression of Nicotinic Alpha 7 Acetylcholine Receptor in Rheumatoid Arthritis and Psoriatic Arthritis", *Scandinavian Journal of Immunology*, vol. 70, 2009, pp. 136-140.

Wilens et al., "Neuronal Nicotinic Receptor Agonists for the Treatment of Attention-Deficit/Hyperactivitt Disorder: Focus on Cognition", *Biochem Pharmacol.*, vol. 74, No. 8, 2007, pp. 1212-1223.

Young et al., "Nicotine Improves Sustained Attention in Mice: Evidence for Involvement of the $\alpha 7$ Nicotinic Acetylcholine Receptor", *Neuropsychopharmacology*, vol. 29, 2004, pp. 891-900.

Young et al., "Impaired attention is central to cognitive deficits observed in alpha 7 deficient mice", *European Neuropsychopharmacology*, vol. 17, 2007, pp. 145-155.

Zhao et al., "Post-Stroke Dementia Nootropic Drug Modulation of Neuronal Nicotinic Acetylcholine Receptors", Annals New York Academy of Sciences, vol. 939, 2001, pp. 179-186.

\* cited by examiner

BIARYL DERIVATIVES AS NACHR MODULATORS

This application is a National Stage Application of PCT/IB2012/053347, filed 2 Jul. 2012, which claims benefit of Serial No. 906/KOL/2011, filed 5 Jul. 2011 in India and which applications are incorporated herein by reference. To the extent appropriate, a claim of priority is made to each of the above disclosed applications.

FIELD OF THE INVENTION

The present invention is related to novel compounds of the general formula (I),

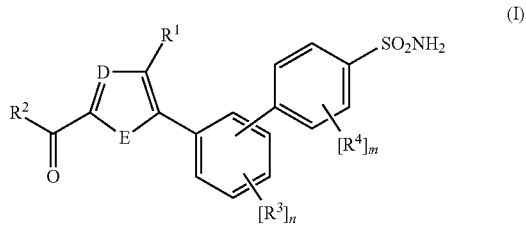

their tautomeric forms, their stereoisomers, their analogues, their prodrugs, their isotopically labeled analogues, their N-oxides, their metabolites, their pharmaceutically acceptable salts, their polymorphs, their solvates, their optical isomers, their clathrates, their co-crystals, their combinations with suitable medicament, pharmaceutical compositions containing them, methods of making the above compounds, and their use as nicotinic acetylcholine receptor α7 subunit (α7 nAChR) modulator.

BACKGROUND OF THE INVENTION

Cholinergic neurotransmission, mediated primarily through the neurotransmitter acetylcholine (ACh), is a predominant regulator of the physiological functions of the body via the central and autonomic nervous system. ACh acts on the synapses of the neurons present in of all the autonomic ganglia, neuromuscular junctions and the central nervous system. Two distinct classes of ACh target receptors viz. muscarinic (mAChRs) and the nicotinic (nAChRs) have been identified in brain, forming a significant component of receptors carrying its mnemonic and other vital physiological functions.

Neural nicotinic ACh receptors (NNRs) belong to the class of ligand-gated ion channels (LGIC) comprising of five subunits (α2-α10, β2-β4) arranged in heteropentameric (α4β2) or homopertameric (α7) configuration (Paterson D et al., Prog. Neurobiol., 2000, 61, 75-111). α4β2 and α7 nAChR constitute the predominant subtypes expressed in the mammalian brain. α7 nAChR has attained prominence as a therapeutic target due to its abundant expression in the learning and memory centers of brain, hippocampus and the cerebral cortex (Rubboli F et al., Neurochem. Int., 1994, 25, 69-71). Particularly, α7 nAChR is characterized by a high $Ca^{2+}$ ion permeability, which is responsible for neurotransmitter release and consequent modulation of excitatory and inhibitory neurotransmission (Alkondon M et al., Eur. J. Pharmacol., 2000, 393, 59-67; Dajas-Bailador F et al., Trends Pharmacol. Sci., 2004, 25, 317-324). Furthermore, high $Ca^{2+}$ ion influx also has implications on the long-term potentiation of memory via alterations in gene expression (Bitner R S et al., J. Neurosci., 2007, 27, 10578-10587; McKay B E et al., Biochem. Pharmacol., 2007, 74, 1120-1133).

Several recent studies have confirmed the role of α7 nAChR in neural processes like attention, memory and cognition (Mansvelder H D et al., Psychopharmacology (Berl), 2006, 184, 292-305; Chan W K et al., Neuropharmacology, 2007, 52, 1641-1649; Young J W et al., Eur. Neuropsychopharmacol., 2007, 17, 145-155). Gene polymorphisms associated with the α7 nAChR protein CHRNA7 have been implicated in the genetic transmission of schizophrenia, related neurophysiological sensory gating deficits and resultant cognitive impairment (Freedman R et al., Biol. Psychiatry, 1995, 38, 22-33; Tsuang D W et al., Am. J. Med. Genet., 2001, 105, 662-668). Also, preclinical studies in α7 nAChR knock-out and anti-sense oligonucleotide treated mice have demonstrated impaired attention and defective cognition underscoring the prominent role of α7 nAChR in cognition (Curzon P et al., Neurosci. Lett., 2006, 410, 15-19; Young J W et al., Neuropsychopharmacology, 2004, 29, 891-900). Additionally, pharmacological blockade of α7 nAChR impairs memory and its activation enhances same in preclinical rodent models implicating α7 nAChR as target for cognitive enhancement (Hashimoto K et al., Biol. Psychiatry, 2008, 63, 92-97).

Pathological brain function in sensory-deficit disorders has been associated with nicotinic cholinergic transmission particularly through α7 receptors (Freedman R et al., Biol. Psychiatry, 1995, 38, 22-33; Tsuang D W et al., Am. J. Med. Genet., 2001, 105, 662-668; Carson R et al., Neuromolecular, 2008, Med. 10, 377-384; Leonard S et al., Pharmacol. Biochem. Behav., 2001, 70, 561-570; Freedman R et al., Curr. Psychiatry Rep., 2003, 5, 155-161; Cannon T D et al., Curr. Opin. Psychiatry, 2005, 18, 135-140). A defective pre-attention processing of sensory information is understood to be the basis of cognitive fragmentation in schizophrenia and related neuropsychiatric disorders (Leiser S C et al., Pharmacol. Ther., 2009, 122, 302-311). Genetic linkage studies have traced sharing of the α7 gene locus for several affective, attention, anxiety and psychotic disorders (Leonard S et al., Pharmacol. Biochem. Behav., 2001, 70, 561-570; Suemaru K et al., Nippon Yakurigaku Zasshi, 2002, 119, 295-300).

Perturbations in the cholinergic and glutamatergic homeostasis, has long been implicated as causative factors for host of neurological disease, including dementia(s) (Nizri E et al., Drug News Perspect., 2007, 20, 421-429). Dementia is a severe, progressive, multi-factorial cognitive disorder affecting memory, attention, language and problem solving. Nicotinic ACh receptor, particularly the interaction of α7 receptor to $αβ_{1-42}$ is implicated as an up-stream pathogenic event in Alzheimer's disease, a major causative factor for dementia (Wang H Y et al., J. Neurosci., 2009, 29, 10961-10973). Moreover, gene polymorphisms in CHRNA7 have been implicated in dementia with lewy bodies (DLB) and Pick's disease (Feher A et al., Dement. Geriatr. Cogn. Disord., 2009, 28, 56-62).

Disease modification potential of nAChRs particularly the α7 receptor has application for disease-modification of Alzheimer's disease (AD) and Parkinson's disease (PD) by enhancing neuron survival and preventing neurodegeneration (Wang et al. 2009; Nagele R G et al., Neuroscience, 2002, 110, 199-211; Jeyarasasingam G et al., Neuroscience, 2002, 109, 275-285). Additionally, α7 nAChR induced activation of anti-apoptotic (BCL-2) and anti-inflammatory pathways in brain could have neuroprotective effects in neurodegenerative diseases (Marrero M B et al., Brain. Res., 2009, 1256, 1-7). Dopamine containing neurons of ventral tegmental area (VTA) and laterodorsal tegmental nucleus (LDT) are known to express nicotinic ACh receptors, particularly α4, α3, β2, β3, β4 subunits (Kuzmin A et al., Psychopharmacology (Berl), 2009, 203, 99-108). Nicotinic ACh receptors, α4β2 and α3β4 have been identified with candidate-gene approach to have strong mechanistic link for nicotine addiction (Weiss R B et al., PLoS Genet., 2008, 4, e1000125). α7 nAChR has particularly been studied for a putative role in cannabis addiction (Solinas M et al., J. Neurosci., 2007, 27, 5615-5620). Varenicline, a partial agonist at α4β2, has demonstrated better efficacy in reducing the smoking addiction and relapse prevention in comparison to buproprion (Ebbert J O et al., Patient. Prefer. Adherence, 2010, 4, 355-362).

Presence of a high-affinity nicotine binding site at α4β2 nAChR, in the descending inhibitory pathways from brainstem has sparked interest in the antinociceptive properties of nicotinic ACh receptor agonists like epibatidine (Decker M W et al., Expert. Opin. Investig. Drugs, 2001, 10, 1819-1830). Several new developments have opened the area for use of nicotinic modulators for therapy of pain (Rowbotham M C et al., Pain, 2009, 146, 245-252). Appropriate modulation of the nicotinic ACh receptors could provide for remedial approach to pain related states.

Another key role of the α7 nAChR is the ability to modulate the production of pro-inflammatory cytokines, like interleukins (IL), tumor necrosis factor alpha (TNF-α), and high mobility group box (HMGB-1) in the central nervous system. Consequently, an anti-inflammatory and antinociceptive effect in pain disorders have been demonstrated (Damaj M I et al., Neuropharmacology, 2000, 39, 2785-2791). Additionally, 'cholinergic anti-inflammatory pathway' is proposed to be a regulatory of local and systemic inflammation and neuroimmune interactions through neural and humoral pathways (Gallowitsch-Puerta M et al., Life Sci., 2007, 80, 2325-2329; Gallowitsch-Puerta and Pavlov, 2007; Rosas-Ballina M et al., Mol. Med., 2009, 15, 195-202; Rosas-Ballina M et al., J. Intern. Med., 2009, 265, 663-679). Selective modulators of nicotinic ACh receptors, particularly α7 type, like GTS-21, attenuate cytokine production and IL-1β after endotoxin exposure. Furthermore, α7 nAChR are understood to have a central role in arthritis pathogenesis and potential therapeutic strategy for treatment of joint inflammation (Westman M et al., Scand. J. Immunol., 2009, 70, 136-140). A putative role for α7 nAChR has also been implicated in severe sepsis, endotoxemic shock and systemic inflammation (Jin Y et al. (2010) Int. J. Immunogenet., Liu C et al., Crit. Care. Med., 2009, 37, 634-641).

Angiogenesis, is a critical physiological process for the cell survival and pathologically important for cancer proliferation; several non-neural nicotinic ACh receptors, particularly α7, α5, α3, β2, β4, are involved (Arias H R et al., Int. J. Biochem. Cell. Biol., 2009, 41, 1441-1451; Heeschen C et al., J. Clin. Invest., 2002, 110, 527-536). A role of nicotinic ACh receptors in the development of cervical cancer, lung carcinogenesis and paediatric lung disorders in smoking-exposed population has also been studied (Calleja-Macias I E et al., Int. J. Cancer, 2009, 124, 1090-1096; Schuller H M et al., Eur. J. Pharmacol., 2000, 393, 265-277). Several α7 nAChR agonists, partial agonists, have been characterized for their efficacy in clinical and preclinical studies. EVP-6124, an agonist at α7 nAChR, has demonstrated significant improvement in sensory processing and cognition biomarkers in Phase Ib study with patients suffering from schizophrenia (EnVivo Pharmaceuticals press release 2009 Jan. 12). GTS-21 (DMXB-Anabaseine), an α7 nAChR agonist, in the P II clinical trials, has shown efficacy in improving cognitive deficits in schizophrenia and inhibition of endotoxin-induced TNF-α release (Olincy A et al., Biol. Psychiatry, 2005, 57 (8, Suppl.), Abst 44; Olincy A et al., Arch. Gen. Psychiatry, 2006, 63, 630-638; Goldstein R et al., Acad. Emerg. Med., 2007, 14 (15, Suppl. 1), Abst 474). CP-810123, a α7 nAChR agonist, exhibits protection against the scopolamine-induced dementia and inhibition of amphetamine-induced auditory evoked potentials in preclinical studies (O'Donnell C J et al., J. Med. Chem., 2010, 53, 1222-1237). SSR-180711A, also an α7 nAChR agonist, enhances learning and memory, and protects against MK-801/Scopolamine-induced memory loss and prepulse inhibition in preclinical studies (Redrobe J P et al., Eur. J. Pharmacol., 2009, 602, 58-65; Dunlop J et al., J. Pharmacol. Exp. Ther., 2009, 328, 766-776; Pichat P et al., Neuropsychopharmacology, 2007, 32, 17-34). SEN-12333, protected against scopolamine-induced amnesia in passive avoidance test in preclinical studies (Roncarati R et al., J. Pharmacol. Exp. Ther., 2009, 329, 459-468). AR-R-17779, an agonist at α7 nAChR, exhibits improvement in the social recognition task performed in rats (Van K M et al., Psychopharmacology (Berl), 2004, 172, 375-383). ABBF, an agonist at α7 nAChR, improves social recognition memory and working memory in Morris maze task in rats (Boess F G et al., J. Pharmacol. Exp. Ther., 2007, 321, 716-725). TC-5619, a selective α7 nAChR agonist has demonstrated efficacy in animal models of positive and negative symptoms and cognitive dysfunction in schizophrenia (Hauser T A et al., Biochem. Pharmacol., 2009, 78, 803-812).

An alternative strategy to reinforce or potentiate the endogenous cholinergic neurotransmission of ACh without directly stimulating the target receptor is the positive allosteric modulation (PAM) of α7 nAChR (Albuquerque E X et al., Alzheimer Dis. Assoc. Disord., 2001, 15 Suppl 1, S19-S25). Several PAMs have been characterized, albeit in the preclinical stages of discovery. A-86774, α7 nAChR PAM, improves sensory gating in DBA/2 mice by significantly reducing the T:C ratio in a preclinical model of schizophrenia (Faghih R et al., J. Med. Chem., 2009, 52, 3377-3384). XY-4083, an α7 nAChR PAM, normalizes the sensorimotor gating deficits in the DBA/2 mice and memory acquisition in 8-arm radial maze without altering the receptor desensitization kinetics (Ng H J et al., Proc. Natl. Acad. Sci., U.S. A., 2007, 104, 8059-8064). Yet another PAM, PNU-120596, profoundly alters α7 nAChR desensitization kinetics and simultaneously protecting against the disruption of prepulse inhibition by MK-801. NS-1738, another PAM, has exhibited efficacy in-vivo in the animal models of social recognition and spatial memory acquisition in the Morris maze task (Timmermann D B et al., J. Pharmacol. Exp. Ther., 2007, 323, 294-307). In addition, several patents/applications published are listed below US 2006/0142349, US 2007/0142450, US 2009/0253691, WO 2007/031440, WO 2009/115547, WO 2009/135944, WO 2009/127678, WO 2009/127679, WO 2009/043780, WO 2009/043784, U.S. Pat. No. 7,683,084, U.S. Pat. No. 7,741,364, WO 2009/145996, US 2010/0240707, WO 2011/064288, US 2010/0222398, US 2010/0227869, EP 1 866 314, WO 2010/130768, WO 2011/036167, US 2010/0190819 disclose efficacy of allosteric modulators of nicotinic ACh receptors and underscoring their therapeutic potential.

SUMMARY OF THE INVENTION

According to one aspect of the present invention there is provided compounds represented by the general formula (I), their tautomeric forms, their stereoisomers, their analogues, their prodrugs, their isotopically substituted analogues, their metabolites, their pharmaceutically acceptable salts, their polymorphs, their solvates, their optical isomers, their clathrates, their co-crystals, their combinations with suitable medicament and pharmaceutical compositions containing them

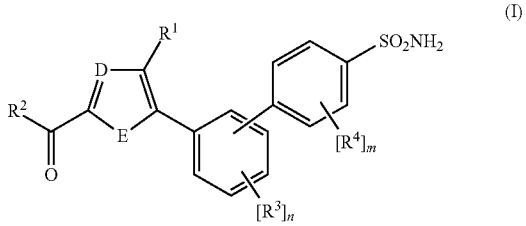

wherein, $R^1$, $R^2$, $R^3$, $R^4$, D, E, m and n are as described hereinbelow.

Thus the present invention further provides a pharmaceutical composition, containing the compound of the general formula (I) as defined herein, its tautomeric forms, its stereoisomers, its analogues, its prodrugs, its isotopically substituted analogues, its metabolites, its pharmaceutically acceptable salts, its polymorphs, its solvates, its optical isomers, its clathrates and its co-crystals in combination with the usual pharmaceutically employed carriers, diluents and the like are useful for the treatment and/or prophylaxis of diseases or disorder or condition such as Alzheimer's disease (AD), mild cognitive impairment (MCI), senile dementia, vascular dementia, dementia of Parkinson's disease, attention deficit disorder, attention deficit hyperactivity disorder (ADHD), dementia associated with Lewy bodies, AIDS dementia complex (ADC), Pick's disease, dementia associated with Down's syndrome, Huntington's disease, cognitive deficits associated with traumatic brain injury (TBI), cognitive decline associated with stroke, poststroke neuroprotection, cognitive and sensorimotor gating deficits associated with schizophrenia, cognitive deficits associated with bipolar disorder, cognitive impairments associated with depression, acute pain, post-surgical or post-operative pain, chronic pain, inflammation, inflammatory pain, neuropathic pain, smoking cessation, need for new blood vessel growth associated with wound healing, need for new blood vessel growth associated with vascularization of skin grafts, and lack of circulation, arthritis, rheumatoid arthritis, psoriasis, Crohn's disease, ulcerative colitis, pouchitis, inflammatory bowel disease, celiac disease, periodontitis, sarcoidosis, pancreatitis, organ transplant rejection, acute immune disease associated with organ transplantation, chronic immune disease associated with organ transplantation, septic shock, toxic shock syndrome, sepsis syndrome, depression, and rheumatoid spondylitis.

The present invention also provides a pharmaceutical composition, containing the compounds of the general formula (I) as defined herein, its tautomeric forms, its stereoisomers, its analogues, its prodrugs, its isotopically substituted analogues, its metabolites, its pharmaceutically acceptable salts, its polymorphs, its solvates, its optical isomers, its clathrates and its co-crystals in combination with the usual pharmaceutically employed carriers, diluents and the like are useful for the treatment and/or prophylaxis of diseases or disorder or condition classified or diagnosed as major or minor neurocognitive disorders, or disorders arising due to neurodegeneration.

The present invention also provides method of administering a compound of formula (I), as defined herein in combination with or as adjunct to medications used in the treatment of attention deficit hyperactivity disorders, schizophrenia, and other cognitive disorders such as Alzheimer's disease, Parkinson's dementia, vascular dementia or dementia associated with Lewy bodies, traumatic brain injury.

The present invention also provides method of administering a compound of formula (I), as defined herein in combination with or as an adjunct to acetylcholinesterase inhibitors, disease modifying drugs or biologics for neurodegenerative disorders, dopaminergic drugs, antidepressants, typical or an atypical antipsychotic.

The present invention also provides use of a compound of formula (I) as defined herein in the preparation of a medicament for treating a disease or disorder or condition selected from the group classified or diagnosed as major or minor neurocognitive disorders, or disorders arising due to neurodegeneration.

The present invention also provides use of a compound of formula (I) as defined herein in the preparation of a medicament for treating a disease or disorder or condition selected from the group consisting of attention deficit hyperactivity disorders, schizophrenia, cognitive disorders, Alzheimer's disease, Parkinson's dementia, vascular dementia or dementia associated with Lewy bodies, and traumatic brain injury.

The present invention also provides use of a compound of formula (I) as defined herein in combination with or as an adjunct to acetylcholinesterase inhibitors, disease modifying drugs or biologics for neurodegenerative disorders, dopaminergic drugs, antidepressants, or a typical or atypical antipsychotic.

DETAILED DESCRIPTION OF THE INVENTION

The present invention relates to novel compounds of the general formula (I), their tautomeric forms, their stereoisomers, their analogues, their prodrugs, their isotopically substituted analogues, their metabolites, their sulfoxides, their N-oxides, their pharmaceutically acceptable salts, their polymorphs, their solvates, their optical isomers, their clathrates, their co-crystals, their combinations with suitable medicament and pharmaceutical compositions containing them,

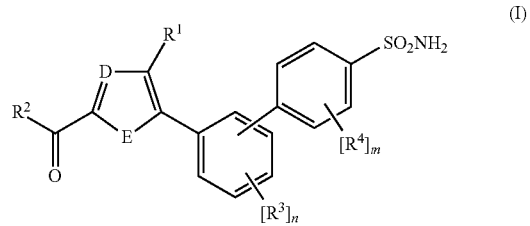

wherein,
'D' is selected from N and $CR^5$;
'E' is selected from S and $NR^6$;
with a proviso that when 'E' is $NR^6$, 'D' is not selected as N;
$R^1$ is selected from hydrogen or substituted- or unsubstituted-alkyl, substituted- or unsubstituted-alkenyl, halogen, perhaloalkyl, substituted- or unsubstituted-cycloalkyl, substituted- or unsubstituted-heterocyclyl, cyano, nitro, $(R^7)(R^8)N—$, $R^{7c}C(=O)N(R^8)—$, $(R^{7a})(R^8)NC(=A^1)N(R^9)—$, $R^{7b}OC(=O)NR^{8a}—$, $R^{7b}SO_2N(R^{8a})—$, $R^7A^1-$, $(R^{7a})(R^8)NC(=O)—$, and $R^{7b}S(O)_p—$, wherein 'p' is an integer ranging from 1 to 2;
$R^2$ is selected from substituted- or unsubstituted-alkyl, substituted- or unsubstituted-alkenyl, substituted- or unsubstituted-cycloalkyl, substituted- or unsubstituted-heterocyclyl, $(R^7)(R^8)N—$, $(R^7)N(OR^{7c})—$, and $R^7A^1-$;

$R^3$ is selected independently at each occurrence from halogen, cyano, substituted- or unsubstituted-alkyl, substituted- or unsubstituted-cycloalkyl, substituted- or unsubstituted-heterocyclyl, $(R^{7a})(R^{8a})NC(=O)$—, $R^{7a}A^1$-, $(R^{7b})C(=O)N(R^{8a})$—, $(R^{7a})(R^{8a})N$—, $(R^{7a})(R^{8a})NC(=A^1)N(R^9)$—, $(R^{7a})(R^{8a})NC(=O)O$—, $R^{7b}OC(=O)N(R^{8a})$—, $R^{7b}S(O)_p$—, wherein 'p' is an integer ranging from 1 to 2, and two $R^3$s and the carbon atoms to which they are attached can combine to form an substituted- or unsubstituted-5 to 8 member cyclic system which may contain 1 to 3 heteroatoms/groups selected from —NH—, —S—, —O—, —C(=O)—, and —C(=S)—;

'n' is selected from 0, 1, 2 and 3;

$R^4$ is selected independently at each occurrence from halogen, cyano, substituted- or unsubstituted-alkyl, substituted- or unsubstituted-cycloalkyl, substituted- or unsubstituted-heterocyclyl, $(R^{7a})(R^{8a})NC(=O)$—, $R^{7a}A^1$-, $(R^{7b})C(=O)N(R^{8a})$—, $(R^{7a})(R^{8a})N$—, and two $R^4$s and the carbon atoms to which they are attached can combine to form a substituted- or unsubstituted-5 to 8 membered cyclic system which may contain 1 to 3 heteroatoms/groups such as —NH—, —S—, —O—, —C(=O)—, and —C(=S)—;

'm' is selected from 0, 1, 2 and 3;

$R^5$ is selected from hydrogen, halogen, substituted- or unsubstituted-alkyl, substituted- or unsubstituted-aryl, substituted- or unsubstituted-heteroaryl, substituted- or unsubstituted-cycloalkyl, substituted- or unsubstituted-heterocyclyl, $(R^7)(R^8)N$—, and $R^{7c}C(=O)$—;

$R^6$ is selected from hydrogen, substituted- or unsubstituted-alkyl, substituted- or unsubstituted-cycloalkyl, and $R^{7c}C(=O)$—;

$R^7$ and $R^8$ are independently selected from hydrogen, substituted- or unsubstituted-alkyl, substituted- or unsubstituted-aryl, substituted- or unsubstituted-heteroaryl, substituted- or unsubstituted-cycloalkyl, and substituted- or unsubstituted-heterocyclyl;

$R^{7a}$, $R^{8a}$, and $R^9$ are independently selected from hydrogen, substituted- or unsubstituted-alkyl, and substituted- or unsubstituted-cycloalkyl;

$R^{7b}$ is selected from substituted- or unsubstituted-alkyl, and substituted- or unsubstituted-cycloalkyl;

$R^{7c}$ is selected from substituted- or unsubstituted-alkyl, substituted- or unsubstituted-aryl, substituted- or unsubstituted-heteroaryl, substituted- or unsubstituted-cycloalkyl, and substituted- or unsubstituted-heterocyclyl;

the substituents on 'alkyl' and 'alkenyl' are selected from the group consisting of oxo, halogen, nitro, cyano, perhaloalkyl, substituted or unsubstituted cycloalkyl, substituted or unsubstituted cycloalkenyl, substituted or unsubstituted aryl, substituted or unsubstituted heteroaryl, substituted or unsubstituted heterocyclyl, $R^{10b}A^1$-, $R^{10a}SO_2$—, $R^{10a}OC(=O)$—, $R^{10a}C(=O)O$—, $R^{10}N(H)C(=O)$—, $R^{10}N(alkyl)C(=O)$—, $R^{10a}C(=O)N(H)$—, $R^{10}N(H)$—, $R^{10}N(alkyl)$-, $R^{10}N(H)C(=A^1)N(H)$—, and $R^{10}N(alkyl)C(=A^1)N(H)$—;

the substituents on 'cycloalkyl' and 'cycloalkenyl' are selected from the group consisting of oxo, halogen, nitro, cyano, substituted or unsubstituted alkyl, substituted or unsubstituted alkenyl, perhaloalkyl, substituted or unsubstituted aryl, substituted or unsubstituted heteroaryl, substituted or unsubstituted heterocyclyl, $R^{10b}A^1$-, $R^{10a}SO_2$—, $R^{10a}C(=O)$—, $R^{10a}OC(=O)$—, $R^{10a}C(=O)O$—, $R^{10}N(H)C(=O)$—, $R^{10}N(alkyl)C(=O)$—, $R^{10a}C(=O)N(H)$—, $R^{10}N(H)$—, $R^{10}N(alkyl)$—, $R^{10}N(H)NC(=A^1)N(H)$—, and $R^{10}N(alkyl)NC(=A^1)N(H)$—;

the substituents on 'aryl' are selected from the group consisting of halogen, nitro, cyano, hydroxy, substituted or unsubstituted alkyl, substituted or unsubstituted alkenyl, perhaloalkyl, substituted or unsubstituted cycloalkyl, substituted or unsubstituted cycloalkenyl, substituted- or unsubstituted-heterocycle, alkyl-O—, perhaloalkyl-O—, alkyl(alkyl)N—, alkyl(H)N—, $H_2N$—, alkyl-$SO_2$—, perhaloalkyl-$SO_2$—, alkyl-C(=O)N(alkyl)-, alkyl-C(=O)N(H)—, alkyl(alkyl)NC(=O)—, alkyl(H)NC(=O)—, $H_2NC(=O)$—, alkyl(alkyl)$NSO_2$—, alkyl(H)$NSO_2$—, and $H_2NSO_2$—;

the substituents on 'heteroaryl' are selected from the group consisting of halogen, nitro, cyano, hydroxy, substituted- or unsubstituted-alkyl, substituted- or unsubstituted-alkenyl, perhaloalkyl, substituted- or unsubstituted-cycloalkyl, substituted- or unsubstituted-cycloalkenyl, substituted- or unsubstituted-heterocycle, alkyl-O—, perhaloalkyl-O—, alkyl(alkyl)N—, alkyl(H)N—, $H_2N$—, alkyl-$SO_2$—, perhaloalkyl-$SO_2$—, alkyl-C(=O)N(alkyl)-, alkyl-C(=O)N(H)—, alkyl(alkyl)NC(=O)—, alkyl(H)NC(=O)—, $H_2NC(=O)$—, alkyl(alkyl)$NSO_2$—, alkyl(H)$NSO_2$—, and $H_2NSO_2$—;

the substituents on ring carbon of 'heterocycle' is selected from the group consisting of halogen, nitro, cyano, oxo, substituted- or unsubstituted-alkyl, substituted- or unsubstituted-alkenyl, perhaloalkyl, substituted- or unsubstituted-cycloalkyl, substituted- or unsubstituted-cycloalkenyl, substituted- or unsubstituted-aryl, substituted- or unsubstituted-heteroaryl, substituted- or unsubstituted-heterocyclyl, substituted- or unsubstituted-alkyl, $R^{10b}A^1$-, —$R^{10a}OC(=O)$—, $R^{10a}C(=O)O$—, $R^{10}(H)NC(=O)$—, $R^{10}N(alkyl)C(=O)$—, $R^{10a}C(=O)N(H)$—, $R^{10}(H)N$—, $R^{10}(alkyl)N$—, $R^{10}(H)NC(=A^1)N(H)$—, and $R^{10}(alkyl)NC(=A^1)N(H)$—;

the substituents on ring nitrogen of 'heterocycle' is selected from the group consisting of substituted- or unsubstituted-alkyl, substituted- or unsubstituted-alkenyl, substituted- or unsubstituted-cycloalkyl, substituted- or unsubstituted-cycloalkenyl, substituted- or unsubstituted-aryl, substituted- or unsubstituted-heteroaryl, $R^{10a}SO_2$—, $R^{10a}C(=O)$—, $R^{10a}OC(=O)$—, $R^{10}(H)NC(=O)$—, and $R^{10}N(alkyl)C(=O)$—;

the "5 to 8 membered cyclic system" is substituted with 1 to 3 substituents selected from the group consisting of halogen, nitro, cyano, aryl, heteroaryl, alkyl, alkenyl, alkynyl, $R^{10a}C(=O)$—, $R^{10a}SO_2$—, $R^{10b}A^1$-, $R^{10a}OC(=O)$—, $R^{10a}C(=O)O$—, $(R^{10})(H)NC(=O)$—, $(R^{10})(alkyl)NC(=O)$—, $R^{10a}C(=O)N(H)$—, $(R^{10})(H)N$—, $(R^{10})(alkyl)N$—, $(R^{10})(H)NC(=A^1)N(H)$—, and $(R^{10})(alkyl)NC(=A^1)N(H)$—;

$R^{10}$ is selected from the group consisting of hydrogen, alkyl, alkenyl, cycloalkyl, cycloalkenyl, aryl, heteroaryl, and heterocyclyl;

$R^{10a}$ is selected from the group consisting of alkyl, alkenyl, perhaloalkyl, cycloalkyl, cycloalkenyl, aryl, heteroaryl, and heterocyclyl;

$R^{10b}$ is selected from the group consisting of hydrogen, alkyl, alkenyl, perhaloalkyl, cycloalkyl, cycloalkenyl, aryl, heteroaryl, and heterocyclyl;

$A^1$ is selected from S and O.

Whenever a range of the number of atoms in a structure is indicated (e.g., a $C_{1-12}$, $C_{1-8}$, $C_{1-6}$, or $C_{1-4}$ alkyl, alkylamino, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

In any of the embodiments of the invention described above, D is selected from the group consisting of CH, C(alkyl), and N.

In any of the embodiments of the invention described above, E is selected from —S— and —N(alkyl)-.

In any of the embodiments of the invention described above, $R^1$ is preferably selected as substituted- or unsubstituted-alkyl.

In any of the embodiments of the invention described above, $R^2$ is preferably selected from substituted- or unsubstituted-alkyl and substituted- or unsubstituted-heterocyclyl.

In any of the embodiments described above, $R^3$ is preferably selected from halogen, $R^{7a}A^1$-, and $(R^{7a})(R^{8a})N$—; and n is preferably selected from 0 and 1.

In any of the embodiments described above, m is preferably selected as 0.

In any of the embodiments described above D is selected from CH, C(alkyl), and N; E is selected from —S— and —N(alkyl)-; $R^1$ is preferably selected as substituted- or unsubstituted-alkyl; $R^2$ is preferably selected from substituted- or unsubstituted-alkyl and substituted- or unsubstituted-heterocyclyl; $R^3$ is preferably selected from halogen, $R^{7a}A^1$-, and $(R^{7a})(R^{8a})N$—; n is preferably selected from 0 and 1; and m is preferably selected as 0.

General terms used in formula can be defined as follows; however, the meaning stated should not be interpreted as limiting the scope of the term per se.

The term "alkyl", as used herein, means a straight chain or branched hydrocarbon containing from 1 to 20 carbon atoms. Preferably the alkyl chain may contain 1 to 10 carbon atoms. More preferably alkyl chain may contain up to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkenyl" as used herein, means an 'alkyl' group as defined hereinabove containing 2 to 20 carbon atoms and containing at least one double bond. Representative examples of alkenyl include, but are not limited to, pent-2-enyl, hex-3-enyl, allyl, venyl, etc.

The term "alkynyl" as used herein, means an 'alkyl' group as defined hereinabove containing 2 to 20 carbon atoms and containing at least one triple bond. Representative examples of alkynyl include, but are not limited to, pent-2-ynyl, hex-3-ynyl, acetylene, etc.

'Alkyl', 'alkenyl' or 'alkynyl' as defined hereinabove may be substituted with one or more substituents selected independently from the group comprising of oxo, halogen, nitro, cyano, aryl, heteroaryl, cycloalkyl, $R^{10a}SO_2$—, $R^{10}A^1$-, $R^{10a}OC(=O)$—, $R^{10a}C(=O)O$—, $(R^{10})(H)NC(=O)$—, $(R^{10})(alkyl)NC(=O)$—, $R^{10a}C(=O)N(H)$—, $(R^{10})(H)N$—, $(R^{10})(alkyl)N$—, $(R^{10})(H)NC(=A^1)N(H)$—, and $(R^{10})(alkyl)NC(=A^1)N(H)$—; wherein $R^{10}$ is selected from hydrogen, alkyl, alkenyl, alkynyl, aryl, heteroaryl, cycloalkyl and heterocyclyl; $A^1$ is selected from S and O; and $R^{10a}$ is selected from alkyl, alkenyl, alkynyl perhaloalkyl, aryl, heteroaryl, cycloalkyl and heterocyclyl.

The term "perhaloalkyl" used herein means an alkyl group as defined hereinabove wherein all the hydrogen atoms of the said alkyl group are substituted with halogen. The perhaloalkyl group is exemplified by trifluoromethyl, pentafluoroethyl and the like.

The term "cycloalkyl" as used herein, means a monocyclic, bicyclic, or tricyclic non-aromatic ring system containing from 3 to 14 carbon atoms, preferably monocyclic cycloalkyl ring containing 3 to 6 carbon atoms. Examples of monocyclic ring systems include cyclopropyl, cyclobutyl, cyclopentyl, cyclohexyl, cycloheptyl, and cyclooctyl. Bicyclic ring systems are also exemplified by a bridged monocyclic ring system in which two non-adjacent carbon atoms of the monocyclic ring are linked by an alkylene bridge. Representative examples of bicyclic ring systems include, but are not limited to, bicyclo[3.1.1]heptane, bicyclo[2.2.1]heptane, bicyclo [2.2.2]octane, bicyclo[3.2.2]nonane, bicyclo[3.3.1]nonane, and bicyclo[4.2.1]nonane, bicyclo[3.3.2]decane, bicyclo [3.1.0]hexane, bicyclo[410]heptane, bicyclo[3.2.0]heptanes, octahydro-1H-indene. Tricyclic ring systems are also exemplified by a bicyclic ring system in which two non-adjacent carbon atoms of the bicyclic ring are linked by a bond or an alkylene bridge. Representative examples of tricyclic-ring systems include, but are not limited to, tricyclo[3.3.1.0$^{3,7}$] nonane and tricyclo[3.3.1.1$^{3,7}$]decane (adamantane). The term cycloalkyl also include spiro systems wherein one of the ring is annulated on a single carbon atom such ring systems are exemplified by spiro[2.5]octane, spiro[4.5]decane, spiro [bicyclo[4.1.0]heptane-2,1'-cyclopentane], hexahydro-2'H-spiro[cyclopropane-1,1'-pentalene].

'Cycloalkyl' as defined hereinabove may be substituted with one or more substituents selected independently from the group comprising of oxo, halogen, nitro, cyano, aryl, heteroaryl, alkyl, alkenyl, alkynyl, $R^{10a}C(=O)$—, $R^{10a}SO_2$—, —$R^{10}A^1$-, $R^{10a}OC(=O)$—, $R^{10a}C(=O)O$—, $(R^{10})(H)NC(=O)$—, $(R^{10})(alkyl)NC(=O)$—, $R^{10a}C(=O)N(H)$—, $(R^{10})(H)N$—, $(R^{10})(alkyl)N$—, $(R^{10})(H)NC(=A^1)N(H)$—, and $(R^{10})(alkyl)NC(=A^1)N(H)$—; wherein $R^{10}$ is selected from hydrogen, alkyl, alkenyl, alkynyl, aryl, heteroaryl, cycloalkyl and heterocyclyl; $A^1$ is selected from S and O; and $R^{10a}$ is selected from alkyl, alkenyl, alkynyl, perhaloalkyl, aryl, heteroaryl, cycloalkyl and heterocyclyl The term "aryl" refers to a monovalent monocyclic, bicyclic or tricyclic aromatic hydrocarbon ring system. Examples of aryl groups include phenyl, naphthyl, anthracenyl, fluorenyl, indenyl, azulenyl, and the like. Aryl group also include partially saturated bicyclic and tricyclic aromatic hydrocarbons such as tetrahydro-naphthalene. The said aryl group also includes aryl rings fused with heteroaryl or heterocyclic rings such as 2,3-dihydro-benzo[1,4]dioxin-6-yl, 2,3-dihydro-benzo[1,4]dioxin-5-yl, 2,3-dihydro-benzofuran-5-yl, 2,3-dihydro-benzofuran-4-yl, 2,3-dihydro-benzofuran-6-yl, 2,3-dihydro-benzofuran-6-yl, 2,3-dihydro-1H-indol-5-yl, 2,3-dihydro-1H-indol-4-yl, 2,3-dihydro-1H-indol-6-yl, 2,3-dihydro-1H-indol-7-yl, benzo[1,3]dioxol-4-yl, benzo[1,3] dioxol-5-yl, 1,2,3,4-tetrahydroquinolinyl, 1,2,3,4-tetrahydroisoquinolinyl, 2,3-dihydrobenzothien-4-yl, 2-oxoindolin-5-yl.

'Aryl' as defined hereinabove may be substituted with one or more substituents selected independently from the group comprising of halogen, nitro, cyano, hydroxy, $C_1$ to $C_6$ alkyl, $C_2$ to $C_6$ alkenyl, $C_2$ to $C_6$ alkynyl, $C_3$ to $C_6$ cycloalkyl, 3- to 6-membered heterocycle, $C_1$ to $C_6$ perhaloalkyl, alkyl-O—, alkenyl-O—, alkynyl-O—, perhaloalkyl-O—, alkyl-N(alkyl)-, alkyl-N(H)—, $H_2N$—, alkyl-$SO_2$—, perhaloalkyl-$SO_2$—, alkyl-C(=O)N(alkyl)-, alkyl-C(=O)N(H)—, alkyl-N(alkyl)C(=O)—, alkyl-N(H)C(=O)—, $H_2NC$(=O)—, alkyl-N(alkyl)$SO_2$—, alkyl-N(H)$SO_2$—, and $H_2NSO_2$—.

The term "heteroaryl" refers to a 5-14 membered monocyclic, bicyclic, or tricyclic ring system having 1-4 ring heteroatoms selected from O, N, or S, and the remainder ring atoms being carbon (with appropriate hydrogen atoms unless otherwise indicated), wherein at least one ring in the ring system is aromatic. Heteroaryl groups may be substituted or unsubstituted with one or more substituents. In one embodiment, 0, 1, 2, 3, or 4 atoms of each ring of a heteroaryl group may be substituted by a substituent. Examples of heteroaryl groups include pyridyl, 1-oxo-pyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, benzoxazolyl, benzofuranyl, indolizinyl, imidazopyridyl, tetrazolyl, benzimidazolyl, benzothiazolyl, benzothiadiazolyl, benzoxadiazolyl, indolyl, azaindolyl, imidazopyridyl, quinazolinyl, purinyl, pyrrolo[2,3]pyrimidinyl, pyrazolo[3,4]pyrimidinyl, and benzo(b)thienyl, 2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl and the like.

'Heteroaryl' as defined hereinabove may be substituted with one or more substituents selected independently from the group comprising of halogen, nitro, cyano, hydroxy, $C_1$ to $C_6$ alkyl, $C_2$ to $C_6$ alkenyl, $C_2$ to $C_6$ alkynyl, $C_3$ to $C_6$ cycloalkyl, 3- to 6-membered heterocycle, $C_1$ to $C_6$ perhaloalkyl, alkyl-O—, alkenyl-O—, alkynyl-O—, perhaloalkyl-O—, alkyl-N(alkyl)-, alkyl-N(H)—, $H_2N$—, alkyl-$SO_2$—, perhaloalkyl-$SO_2$—, alkyl-C(=O)N(alkyl)-, alkyl-C(=O)N(H)—, alkyl-N(alkyl)C(=O)—, alkyl-N(H)C(=O)—, $H_2NC$(=O)—, alkyl-N(alkyl)$SO_2$—, alkyl-N(H)$SO_2$—, and $H_2NSO_2$—.

The term "heterocycle" or "heterocyclic" as used herein, means a 'cycloalkyl' group wherein one or more of the carbon atoms replaced by —O—, —S—, —S($O_2$)—, —S(O)—, —N($R'''$)—, —Si($R'''$)$R''$—, wherein, $R'''$ and $R''$ are independently selected from hydrogen, alkyl, alkenyl, alkynyl, aryl, heteroaryl, cycloalkyl, and heterocyclyl. The heterocycle may be connected to the parent molecular moiety through any carbon atom or any nitrogen atom contained within the heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. Representative examples of bicyclic heterocycle include, but are not limited to 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl and 1,2,3,4-tetrahydroquinolinyl. The term heterocycle also include bridged heterocyclic systems such as azabicyclo[3.2.1]octane, azabicyclo[3.3.1]nonane and the like.

'Heterocyclyl' group may be substituted on ring carbons with one or more substituents selected independently from the group comprising of oxo, halogen, nitro, cyano, aryl, heteroaryl, alkyl, alkenyl, alkynyl, $R^{10}A^1$-, $R^{10a}OC$(=O)—, $R^{10a}C$(=O)O—, $(R^{10})(H)NC$(=O)—, $(R^{10})$(alkyl)NC(O)—, $R^{10a}C$(=O)N(H)—, $(R^{10})(H)N$—, $(R^{10})$(alkyl)N—, $(R^{10})(H)NC$(=$A^1$)N(H)—, and $(R^{10})$(alkyl)NC(=$A^1$)N(H)—; wherein $R^{10}$ is selected from hydrogen, alkyl, alkenyl, alkynyl, aryl, heteroaryl, cycloalkyl and heterocyclyl; $A^1$ is selected from S and O; and $R^{10a}$ is selected from alkyl, alkenyl, alkynyl, perhaloalkyl, aryl, heteroaryl, cycloalkyl and heterocyclyl.

'Heterocyclyl' group may further be substituted on ring nitrogen(s) with substituents selected from the group comprising of aryl, heteroaryl, alkyl, alkenyl, alkynyl, $R^{10a}C$(=O)—, $R^{10a}SO_2$—, $R^{10a}OC$(=O)—, $(R^{10})(H)NC$(=O)—, $(R^{10})$(alkyl)NC(=O)—; wherein $R^{10}$ is selected from hydrogen, alkyl, alkenyl, alkynyl, aryl, heteroaryl, cycloalkyl and heterocyclyl; $R^{10a}$ is selected from alkyl, alkenyl, alkynyl, perhaloalkyl, aryl, heteroaryl, cycloalkyl and heterocyclyl.

The term 'oxo' means a divalent oxygen (=O) attached to the parent group. For example oxo attached to carbon forms a carbonyl, oxo substituted on cyclohexane forms a cyclohexanone, and the like.

The term 'annulated' means the ring system under consideration is either annulated with another ring at a carbon atom of the cyclic system or across a bond of the cyclic system as in the case of fused or spiro ring systems.

The term 'bridged' means the ring system under consideration contain an alkylene bridge having 1 to 4 methylene units joining two non adjacent ring atoms.

A compound, its stereoisomers, racemates, and pharmaceutically acceptable salt thereof as described hereinabove wherein the compound of general formula (I) is selected from:
2'-Methoxy-5'-(3-methyl-5-propionylthiophen-2-yl)-[1,1'-biphenyl]-4-sulfonamide (Compound 1);
2'-chloro-5'-(3-methyl-5-propionylthiophen-2-yl)-[1,1'-biphenyl]-4-sulfonamide (Compound 2);
3'-(3-methyl-5-propionylthiophen-2-yl)-[1,1'-biphenyl]-4-sulfonamide (Compound 3);
2'-(dimethylamino)-5'-(3-methyl-5-propionylthiophen-2-yl)-[1,1'-biphenyl]-4-sulfonamide (Compound 4);
2'-methoxy-5'-(4-methyl-2-(piperidine-1-carbonyl)thiazol-5-yl)-(1,1'-biphenyl)-4-sulfonamide (Compound 5);
2'-methoxy-5'-(4-methyl-2-(pyrrolidine-1-carbonyl)thiazol-5-yl)-(1,1'-biphenyl)-4-sulfonamide (Compound 6);
2'-chloro-5'-(4-methyl-2-(pyrrolidine-1-carbonyl)thiazol-5-yl)-(1,1'-biphenyl)-4-sulfonamide (Compound 7);
2'-methoxy-5'-(4-methyl-2-propionylthiazol-5-yl)-[1,1'-biphenyl]-4-sulfonamide (Compound 8);
5'-(3,4-dimethyl-5-propionylthiophen-2-yl)-2'-methoxy-[1,1'-biphenyl]-4-sulfonamide (Compound 9);
5'-(1,3-dimethyl-5-propionyl-1H-pyrrol-2-yl)-2'-methoxy-(1,1'-biphenyl)-4-sulfonamide (Compound 10).

According to another aspect of the present invention, the compounds of general formula (I) where all the symbols are as defined earlier were prepared by methods described below. However, the invention is not limited to these methods; the compounds may also be prepared by using procedures described for structurally related compounds in the literature.

SCHEME-1

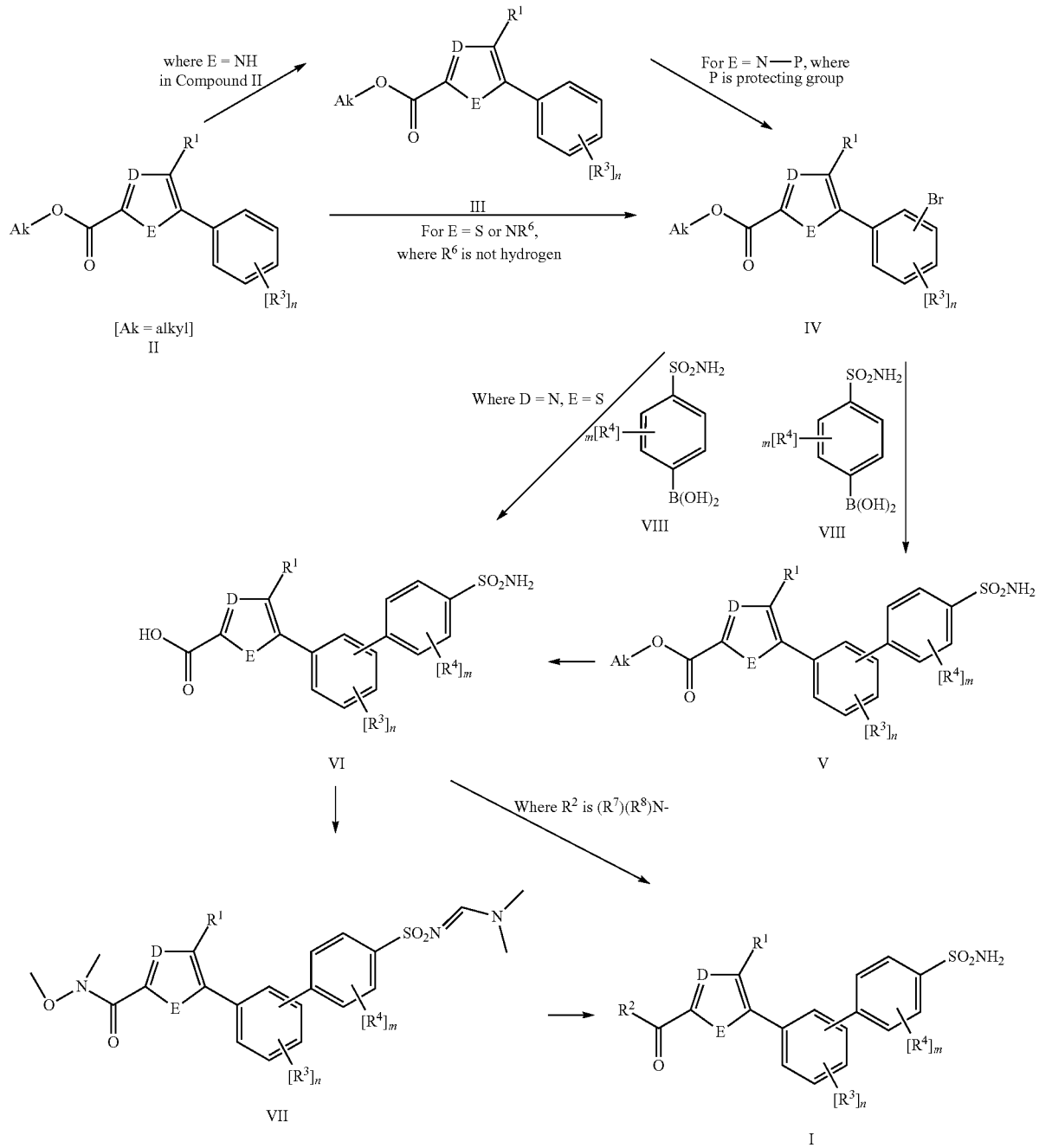

Scheme 1 provides a route for preparation of the compound of the formula (I), where $R^1$, $R^2$, $R^3$, $R^4$, m, n, D and E are same as defined earlier, from compound of formula (II), where $R^1$, $R^3$, n, E and D are same as defined under generic formula (I).

Compound of formula (II) can be prepared by the procedures described in the literature such as U.S. Pat. No. 5,608,082; WO 2007/092751, Organic Letters, 9, 25, 2007, 5191-5194; WO 2006/89076, WO 2005/42540, WO 2008/036541, or methods well known to the person skilled in the art.

The compound of formula (II), where E is selected from S and $NR^6$, where $R^6$ is substituted- or unsubstituted-alkyl, substituted- or unsubstituted-cycloalkyl, or $R^{7c}C(=O)$—, D is selected from $CR^5$ and N, and $R^1$, $R^3$ and n are as defined under general formula (I), on bromination gives compound of formula IV, where all the symbols are the same as defined earlier for compound of formula II.

The compound of formula (II), where E is $NR^6$, where $R^6$ hydrogen, and $R^3$, n and D are same as defined under generic formula (I), reacted with a suitable amino protecting reagent as described in Greene and Wuts (protective groups in Organic Synthesis, Wiley and sons, 1999) to obtain compound of formula (III), where E is N—P, where P is a protecting group, and $R^3$, n and D are same as defined under generic formula (I). Protecting groups 'P', may be selected form but not limited to tert-butoxycarbonyl (Boc), benzyloxycarbonyl (Cbz), benzyl (Bn), acetyl and trifluoroacetyl.

The compound of the formula (III), where E is P, where P is a protecting group, and $R^1$, $R^3$, n and D are same as defined under generic formula (I), on bromination gives compound of formula (IV), where E is P, where P is a protecting group, and $R^1$, $R^3$, n and D are same as defined under generic formula (I). Bromination can be carried out under a condition generally used in the synthetic organic chemistry using brominating agents such as N-bromosuccinimide, bromine, phosphorous tribromide and aluminium tribromide. The inventors have carried out bromination using bromine in acetic acid.

Alternatively, the bromo compound of formula (IV), where all the symbols are the same as defined earlier can be prepared by reduction of nitro group of corresponding nitro-derivative of compound of formula (II) or (III) to amino group using procedure provided in Tetrahedron, 2008, 64, 6406-6414. The said amino group can then be converted to diazonium compound using a condition usually applied for diazotization, i.e. by treating corresponding amino compound with nitrite e.g. tert-butyl nitrite. The diazo-compound can then subsequently was treated with copper halide preferably copper(II)bromide or bromoform to obtain compound of formula (IV) under standard Sandmeyer condition as provided in WO 2007/125934.

The compound of formula (IV), where $R^1$, $R^3$ and n are same as defined under general formula (I), and D is $CR^5$, and E is S or $NR^6$, where $R^6$ is P, substituted- or unsubstituted-alkyl, substituted- or unsubstituted-cycloalkyl, or $R^{7c}C(=O)$—, was subjected to Suzuki coupling with compound of formula (VIII), where $R^4$ and m as defined under generic formula (I), to obtain compound of formula (V), where $R^1$, $R^3$, $R^4$, m and n are same as defined under general formula (I), and D is $CR^5$, and E is S or $NR^6$, where $R^6$ is P, substituted- or unsubstituted-alkyl, substituted- or unsubstituted-cycloalkyl, or $R^{7c}C(=O)$—. Suzuki coupling can be carried out under different coupling conditions with boronic acids and boronic esters well known in the art. Preferably, the Suzuki coupling is carried out in a mixture of water, ethanol, methanol and toluene in presence of base such as potassium phosphate, potassium carbonate or the like, and a palladium catalyst such as tetrakis(triphenylphosphine)palladium(0) at an temperature of about 50° C. or higher temperature. Boronic acid used in this reaction can be prepared by the methods well known in the art by hydrolysing the corresponding boronate. Boronates are generally commercially available. Besides, such boronates can also be prepared by reacting an appropriate iodo- or bromo compound with an alkyl lithium such as butyl lithium and then reacting with a borate ester or by methods well known in the art (EP 1 012 142; Review article by N. Miyaura and A. Suzuki, Chem. Rev., 1995, 95, 2547).

Hydrolysis of compound of formula (V) gave compound of formula (VI), where $R^1$, $R^3$, $R^4$, m, n, D and E are same as defined earlier for compound of formula (V). Ester hydrolysis may be carried out using standard procedure generally used in synthetic organic chemistry or well known in the art with reagents such as sodium hydroxide, potassium hydroxide, lithium hydroxide or the like in solvents such as water, alcohol, THF or the like or mixtures thereof. Preferably aqueous solution of sodium hydroxide and ethanol were used for the reaction.

Compound of formula (IV), where $R^1$, $R^3$ and n are same as defined under general formula (I), and E is S, and D is N as obtained in the previous step, on Suzuki condition with compound of formula (VIII) gives compound of formula (VI) directly.

The compounds of formula (VI) where $R^1$, $R^3$, $R^4$, m and n are same as defined earlier for compound of formula (V), D is $CR^5$, and E is S, can be converted to acid chloride using oxalyl chloride in dichloromethane and DMF followed by reaction with N,O-dimethylhydroxylamine hydrochloride in presence of triethylamine in dichloromethane to provide compounds of formula (VII), where $R^1$, $R^3$, $R^4$, m and n are same as defined earlier for compound of formula (V), and D is $CR^5$, and E is S.

The compounds of formula (VI), where $R^1$, $R^3$, $R^4$, m and n are same as defined under compound of formula (V), D is N when E is S, and D is $CR^5$ when E is $NR^6$, were converted to compounds of formula (VII) by coupling reaction followed by sulfonamide protection. The coupling reaction can be carried out following the conditions generally used for converting carboxylic acids to amides. The reaction can be carried out preferably with N,O-dimethylhydroxylamine hydrochloride and triethylamine in DMF using reagents such as 1-(3-dimethylaminopropyl)-3-ethylcarbodimide hydrochloride (EDCI), benzotriazole hydrate (HOBT) or the like. Sulfonamide protection can be carried out under a condition known to a person skilled in the art or by utilizing the teaching provided in Organic Preparations and Procedures International, 2002, 37(5), 545-549. Inventors have protected sulfonamide using N,N-dimethylformamide dimethyl acetal in presence of DMF to provide compound of formula (VII).

The compound of the formula (VII) is reacted with Grignard reagent $R^2MgX^1$ where $R^2$ is substituted- or unsubstituted-alkyl, substituted- or unsubstituted-alkenyl, substituted- or unsubstituted-cycloalkyl, substituted- or unsubstituted-heterocyclyl, and $X^1$ is a halogen, to obtain the compounds of formula I, where $R^2$ is selected from substituted- or unsubstituted-alkyl, substituted- or unsubstituted-alkenyl, substituted- or unsubstituted-cycloalkyl, substituted- or unsubstituted-heterocyclyl. The reaction of compound of formula (VII) with $R^2MgX^1$ can be carried out according to the procedure given in literature such as J. Med. Chem., 2009, 52, 3377.

Compounds of formula (I), where $R^6$ is selected as hydrogen, can be prepared by deprotecting the protective group used, by following an appropriate procedure as provided in Greene and Wuts (protective groups in Organic Synthesis, Wiley and sons, 1999).

Compound of formula (VI) is alternatively reacted with $(R^7)(R^8)NH$, $(R^7)(OR^{7b})NH$, or $R^7OH$, where $R^7$ and $R^8$ are as defined under definition of $R^2$ in general formula (I), to obtain compound of formula (I), where $R^2$ is selected from the group consisting of $(R^7)(R^8)N$—, $(R^7)(OR^{7b})N$—, and $R^7O$—, wherein $R^7$ and $R^8$ are as defined under definition of $R^2$ in general formula (I). The reaction was carried out according to the conditions known in converting carboxylic acids to amides and esters as known to one skilled in the art. The reaction may be carried out in the presence of solvents, for example, DMF, THF, a halogenated hydrocarbon such as chloroform and dichloromethane, an aromatic hydrocarbon such as xylene, benzene, toluene, or mixtures thereof or the like, in the presence of suitable base such as triethylamine, diisopropylethylamine, pyridine or the like at a temperature between 0-50° C. using reagents such as 1-(3-dimethylaminopropyl)-3-ethylcarbodimide hydrochloride (EDCI), 1,3-dicyclohexylcarbodiimide (DCC), and auxiliary reagents such as 1-hydroxy-7-azabenzotriazole (HOAT), hydroxybenzotriazole hydrate (HOBT) or the like.

Groups covered under R¹ can be introduced in any of the steps of scheme 1 using general group transformation method.

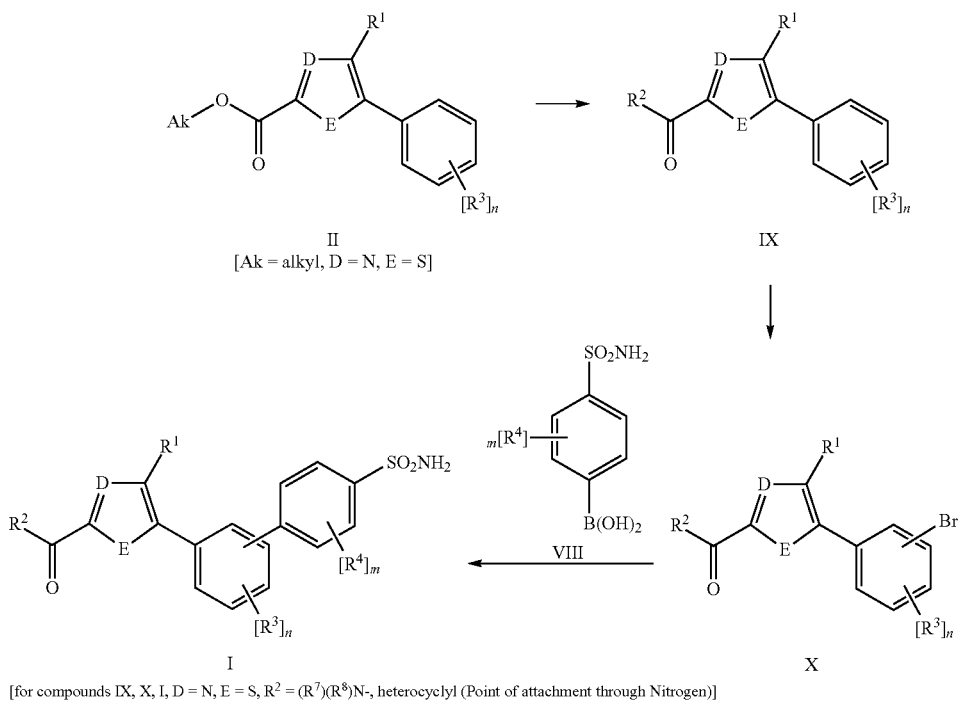

SCHEME-2

II
[Ak = alkyl, D = N, E = S]

IX

I

X

[for compounds IX, X, I, D = N, E = S, R² = (R⁷)(R⁸)N-, heterocyclyl (Point of attachment through Nitrogen)]

Scheme 2 provides a route for preparation of compound of formula (I), where $R^2$ is $(R^7)(R^8)N-$, heterocycle wherein point of attachment is through Nitrogen, D=N, E=S, $R^1$, $R^3$, $R^4$, m and n are same as described under compound of formula (I), from compound of formula (II) where D=N and E=S, $R^1$, $R^3$ and n are same as defined under compound of formula (I).

Compound of formula (II), where D=N and E=S, $R^1$, $R^3$ and n are same as defined under compound of formula (I), can be prepared by the procedure described in the literature such as WO 2006/89076, or methods well known to the person skilled in the art.

Compound of the formula (II) was reacted with $(R^7)(R^8)$NH or heterocycle containing at least one nitrogen in an organic solvent such as ethanol at a temperature ranging between about 20° C. and about 100° C. to obtain a compounds of formula (IX), where $R^2$ is $(R^7)(R^8)N-$, D=N, E=S, and $R^1$, $R^3$ and n are same as defined under compound of formula (I).

The compound of formula (IX), as obtained in the previous step was further brominated by using procedures described hereinabove to obtain compounds of formula (X). The compound of formula (X) so obtained was further subjected to Suzuki coupling with compound of formula (VIII) using the procedures described hereinabove to obtain compound of formula (I).

The term 'room temperature' denotes any temperature ranging between about 20° C. to about 40° C., except and otherwise it is specifically mentioned in the specification.

The intermediates and the compounds of the present invention may obtained in pure form in a manner known per se, for example, by distilling off the solvent in vacuum and re-crystallizing the residue obtained from a suitable solvent, such as pentane, diethyl ether, isopropyl ether, chloroform, dichloromethane, ethyl acetate, acetone or their combinations or subjecting it to one of the purification methods, such as column chromatography (e.g., flash chromatography) on a suitable support material such as alumina or silica gel using eluent such as dichloromethane, ethyl acetate, hexane, methanol, acetone and their combinations. Preparative LC-MS method is also used for the purification of molecules described herein.

Salts of compound of formula (I) can be obtained by dissolving the compound in a suitable solvent, for example in a chlorinated hydrocarbon, such as methyl chloride or chloroform or a low molecular weight aliphatic alcohol, for example, ethanol or isopropanol, which was then treated with the desired acid or base as described in Berge S. M. et al. "Pharmaceutical Salts, a review article in Journal of Pharmaceutical sciences volume 66, page 1-19 (1977)" and in handbook of pharmaceutical salts properties, selection, and use by P. H. Einrich Stahland Camille G.wermuth, Wiley-VCH (2002). Lists of suitable salts can also be found in *Remington's Pharmaceutical Sciences,* 18th ed., Mack Publishing Company, Easton, Pa., 1990, p. 1445, and *Journal of Pharmaceutical Science,* 66, 2-19 (1977). For example, they can be a salt of an alkali metal (e.g., sodium or potassium), alkaline earth metal (e.g., calcium), or ammonium of salt.

The compound of the invention or a composition thereof can potentially be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, potassium hydroxide. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

The stereoisomers of the compounds of formula (I) of the present invention may be prepared by stereospecific syntheses or resolution of the achiral compound using an optically active amine, acid or complex forming agent, and separating the diastereomeric salt/complex by fractional crystallization or by column chromatography.

The term "prodrug" denotes a derivative of a compound, which derivative, when administered to warm-blooded animals, e.g. humans, is converted into the compound (drug). The enzymatic and/or chemical hydrolytic cleavage of the compounds of the present invention occurs in such a manner that the proven drug form (parent carboxylic acid drug) is released, and the moiety or moieties split off remain nontoxic or are metabolized so that nontoxic metabolic products are produced. For example, a carboxylic acid group can be esterified, e.g., with a methyl group or ethyl group to yield an ester. When an ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound.

The prodrugs can be prepared in situ during the isolation and purification of the compounds, or by separately reacting the purified compound with a suitable derivatizing agent. For example, hydroxy groups can be converted into esters via treatment with a carboxylic acid in the presence of a catalyst. Examples of cleavable alcohol prodrug moieties include substituted or unsubstituted, branched or unbranched lower alkyl ester moieties, e.g., ethyl esters, lower alkenyl esters, di-lower alkylamino lower-alkyl esters, e.g., dimethylaminoethyl ester, acylamino lower alkyl esters, acyloxy lower alkyl esters (e.g., pivaloyloxymethyl ester), aryl esters, e.g., phenyl ester, aryl-lower alkyl esters, e.g., benzyl ester, substituted or unsubstituted, e.g., with methyl, halo, or methoxy substituents aryl and aryl-lower alkyl esters, amides, lower-alkyl amides, di-lower alkyl amides, and hydroxy amides.

Modulation of the nicotinic cholinergic receptors, particularly α7 may provide for efficacy in a range of cognitive states, right from pre-attention to attention and subsequently working, reference and recognition memory. Accordingly, this invention may find application in the treatment and prophylaxis of multitude of disease conditions including, either one or combinations of, schizophrenia, schizophreniform disorder, cognitive deficits in schizophrenia, brief psychotic disorder, delusional disorder, schizoaffective disorder, shared psychotic disorder, paranoid personality disorder, schizoid personality disorder, schizotypal personality disorder, attention deficit disorder, attention deficit hyperactivity disorder, depression, maniac depression, major depressive disorder, posttraumatic stress disorder, generalized anxiety disorder, tourette's syndrome, cyclothymic disorder, dysthymic disorder, agoraphobia, panic disorder (with or without agoraphobia), phobias (including social phobia) and bipolar disorders (Thomsen M S et al., Curr. Pharm. Des., 2010, 16, 323-343; Peng Z Z et al., Zhonghua Yi Xue Yi Chuan Xue Za Zhi, 2008, 25, 154-158; Young J W et al., Eur. Neuropsychopharmacol., 2007, 17, 145-155; Martin L F et al., Am. J. Med. Genet., B Neuropsychiatr. Genet., 2007, 144B, 611-614; Martin L F et al., Psychopharmacology (Berl), 2004, 174, 54-64; Feher A et al., Dement. Geriatr. Cogn. Disord., 2009, 28, 56-62; Wilens T E et al., Biochem. Pharmacol., 2007, 74, 1212-1223; Verbois S L et al., Neuropharmacology, 2003, 44, 224-233; Sanberg P R et al., Pharmacol. Ther., 1997, 74, 21-25). Cholinergic system, particularly through α7 nAChR seems to have implications in traumatic brain injury-induced psychosis. Chronic nicotine treatment has shown to attenuate same. Thus, this invention may also find application in the treatment of deficits in cholinergic α7 nAChR following traumatic brain injury (Bennouna M et al., Encephale, 2007, 33, 616-620; Verbois S L et al., Neuropharmacology, 2003, 44, 224-233).

Modulation of nicotinic ACh receptors, particularly the α7 subtype could also help supplement the down-regulated cholinergic receptor expression and transmission as in dementia(s), and also slowing disease progression by reduction of α7-αβ$_{1-42}$ complexation and internalization in AD and Down's syndrome (Nordberg A et al., Neurotox. Res., 2000, 2, 157-165; Haydar S N et al., Bioorg. Med. Chem., 2009, 17, 5247-5258; Deutsch S I et al., Clin. Neuropharmacol., 2003, 26, 277-283).

Appropriately, this invention may find application in the treatment and prophylaxis of multitude of disease conditions including, either one or combinations of, dementia(s) due to Alzheimer's disease, dementia with Lewy bodies, Down's syndrome, head trauma, Stroke, hypoperfusion, Parkinson's disease, Huntington's disease, Prion diseases, progressive supranuclear palsy, radiation therapy, brain tumors, normal-pressure hydrocephalus, subdural hematoma, human immunodeficiency virus (HIV) infection, vitamin deficiency, hypothyroidism, drugs, alcohol, lead, mercury, aluminium, heavy metals, syphilis, Lyme disease, viral encephalitis, fungal infection and cryptococcosis (Zhao X et al., Ann. N.Y. Acad. Sci., 2001, 939, 179-186; Perry E et al., Eur. J. Pharmacol., 2000, 393, 215-222; Harrington C R et al., Dementia, 1994, 5, 215-228; Wang J et al., J. Neurosci. Res., 2010, 88, 807-815; Duris K et al., Stroke 2011, 42(12), 3530-6). Thus, this invention may also find application in the prophylaxis and preventive measures immediately after early-stage identification of neurodegenerative disease like Alzheimer's disease and Parkinson's disease.

Modulation of nicotinic ACh receptors particularly α4β2, α3β4 and α7 may have implications in the development of therapies for nicotine, cannabis addiction and relapse prevention. Accordingly, this invention may find application in the prophylaxis or therapy of nicotine addiction, cannabis addiction, and relapse-prevention of nicotine or cannabis addiction. Additionally, this invention may also provide for an alternative therapy for non-responding addiction patients, patients having intolerable side-effects with de-addiction therapies or those requiring long-term maintenance therapies. (Kuzmin A et al., Psychopharmacology (Berl), 2009, 203, 99-108; Weiss R B et al., PLoS Genet., 2008, 4, e1000125; Solinas M et al., J. Neurosci., 2007, 27, 5615-5620; Ebbert J O et al., Patient. Prefer. Adherence, 2010, 4, 355-362).

This invention may also find application in the treatment and prophylaxis of multitude of pain conditions including, either one or combinations of, pain arising from, peripheral nervous system (PNS), post-diabetic neuralgia (PDN), post-herpetic neuralgia (PHN), multiple sclerosis, Parkinson's disease, low-back pain, fibromyalgia, post-operative pain, acute pain, chronic pain, mononeuropathy, primary lateral sclerosis, pseudobulbar palsy, progressive muscular palsy, progressive bulbar palsy, postpolio syndrome, diabetes induced polyneuropathy, acute demyelinating polyneuropathy (Guillain-Barre syndrome), acute spinal muscular atrophy (Werdnig-Hoffman disease) and secondary neurodegeneration (Donnelly-Roberts D L et al., J. Pharmacol. Exp. Ther., 1998, 285, 777-786; Rowley T J et al., Br. J. Anaesth., 2010, 105, 201-207; Bruchfeld A et al., J. Intern. Med., 2010, 268, 94-101).

This invention may find application in the treatment and prophylaxis of plethora of inflammation and pain related states involving TNF-α and thus providing symptomatic relief in either any one or combination of, rheumatoid arthritis, bone resorption diseases, atherosclerosis, inflammatory bowel disease, Crohn's disease, inflammation, cancer pain, muscle degeneration, osteoarthritis, osteoporosis, ulcerative colitis, rhinitis, pancreatitis, spondylitis, acute respiratory distress syndrome (ARDS), joint inflammation, anaphylaxis, ischemia reperfusion injury, multiple sclerosis, cerebral malaria, septic shock, tissue rejection of graft, brain trauma, toxic shock syndrome, herpes virus infection (HSV-1 & HSV-2), herpes zoster infection, sepsis, fever, myalgias, asthma, uveititis, contact dermatitis, obesity-related disease and endotoxemia (Giebelen I A T et al., Shock, 2007, 27, 443-447; Pena G et al., Eur. J. Immunol., 2010, 40, 2580-2589).

Thus the present invention further provides a pharmaceutical composition, containing the compounds of the general formula (I) as defined above, its tautomeric forms, its stereoisomers, its analogues, its prodrugs, its isotopically substituted analogues, its metabolites, its pharmaceutically acceptable salts, its polymorphs, its solvates, its optical isomers, its clathrates and its co-crystals in combination with the usual pharmaceutically acceptable carriers, diluents and the like.

The pharmaceutically acceptable carrier (or excipient) is preferably one that is chemically inert to the compound of the invention and one that has no detrimental side effects or toxicity under the conditions of use. Such pharmaceutically acceptable carriers preferably include saline (e.g., 0.9% saline), Cremophor EL (which is a derivative of castor oil and ethylene oxide available from Sigma Chemical Co., St. Louis, Mo.) (e.g., 5% Cremophor EL/5% ethanol/90% saline, 10% Cremophor EL/90% saline, or 50% Cremophor EL/50% ethanol), propylene glycol (e.g., 40% propylene glycol/10% ethanol/50% water), polyethylene glycol (e.g., 40% PEG 400/60% saline), and alcohol (e.g., 40% ethanol/60% water). A preferred pharmaceutical carrier is polyethylene glycol, such as PEG 400, and particularly a composition comprising 40% PEG 400 and 60% water or saline. The choice of carrier will be determined in part by the particular compound chosen, as well as by the particular method used to administer the composition. Accordingly, there is a wide variety of suitable formulations of the pharmaceutical composition of the present invention.

The following formulations for oral, aerosol, parenteral, subcutaneous, intravenous, intraarterial, intramuscular, interperitoneal, rectal, and vaginal administration are merely exemplary and are in no way limiting.

The pharmaceutical compositions can be administered parenterally, e.g., intravenously, intra-arterially, subcutaneously, intradermally, intrathecally, or intramuscularly. Thus, the invention provides compositions for parenteral administration that comprise a solution of the compound of the invention dissolved or suspended in an acceptable carrier suitable for parenteral administration, including aqueous and non-aqueous, isotonic sterile injection solutions.

Overall, the requirements for effective pharmaceutical carriers for parenteral compositions are well known to those of ordinary skill in the art. See *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986). Such compositions include solutions containing antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol (for example in topical applications), or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, and synthetic oils. Specific examples of oils useful in such formulations include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl-β-aminopropionates, and 2-alkyl-imidazoline quaternary ammonium salts, and (e) mixtures thereof.

The parenteral formulations typically will contain from about 0.5% or less to about 25% or more by weight of a compound of the invention in solution. Preservatives and buffers can be used. In order to minimize or eliminate irritation at the site of injection, such compositions can contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Topical formulations, including those that are useful for transdermal drug release, are well known to those of skill in the art and are suitable in the context of the present invention for application to skin.

Formulations suitable for oral administration can consist of (a) liquid solutions, such as an effective amount of a compound of the invention dissolved in diluents, such as water, saline, or orange juice; (b) capsules, sachets, tablets, lozenges, and troches, each containing a pre-determined amount of the compound of the invention, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the compound ingredient in a flavor, usually sucrose and acacia or tragacanth, as well as pastilles comprising a compound of the invention in an inert base, such as gelatin and glycerin, or sucrose and acacia, emulsions, gels, and the like containing, in addition to the compound of the invention, such excipients as are known in the art.

A compound of the present invention, alone or in combination with other suitable components, can be made into aerosol formulations to be administered via inhalation. A compound or epimer of the invention is preferably supplied in finely divided form along with a surfactant and propellant. Typical percentages of the compounds of the invention can be about 0.01% to about 20% by weight, preferably about 1% to about 10% by weight. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute from about 0.1% to about 20% by weight of the composition, preferably from about 0.25% to about 5%. The balance of the composition is ordinarily propellant. A carrier can also be included as desired, e.g., lecithin, for intranasal delivery. These aerosol formulations can be placed into acceptable pressurized propellants, such as dichlorodifluoromethane, propane, nitrogen, and the like. They also can be formulated as pharmaceuticals for non-pressured preparations, such as in a nebulizer or an atomizer. Such spray formulations can be used to spray mucosa.

Additionally, the compound of the invention can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the compound ingredient, such carriers as are known in the art to be appropriate.

The concentration of the compound in the pharmaceutical formulations can vary, e.g., from less than about 1% to about 10%, to as much as 20% to 50% or more by weight, and can be selected primarily by fluid volumes, and viscosities, in accordance with the particular mode of administration selected.

For example, a typical pharmaceutical composition for intravenous infusion could be made up to contain 250 ml of sterile Ringer's solution, and 100 mg of at least one compound of the invention. Actual methods for preparing parenterally administrable compounds of the invention will be known or apparent to those skilled in the art and are described in more detail in, for example, *Remington's Pharmaceutical Science* (17th ed., Mack Publishing Company, Easton, Pa., 1985).

It will be appreciated by one of ordinary skill in the art that, in addition to the aforedescribed pharmaceutical compositions, the compound of the invention can be formulated as inclusion complexes, such as cyclodextrin inclusion complexes, or liposomes. Liposomes can serve to target a compound of the invention to a particular tissue, such as lymphoid tissue or cancerous hepatic cells. Liposomes can also be used to increase the half-life of a compound of the invention. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837,028, and 5,019,369.

The compounds or pharmaceutical compositions are useful, in an embodiment, for the treatment and/or prophylaxis of diseases or disorder or condition such as Alzheimer's disease (AD), mild cognitive impairment (MCI), senile dementia, vascular dementia, dementia of Parkinson's disease, attention deficit disorder, attention deficit hyperactivity disorder (ADHD), dementia associated with Lewy bodies, AIDS dementia complex (ADC), Pick's disease, dementia associated with Down's syndrome, Huntington's disease, cognitive deficits associated with traumatic brain injury (TBI), cognitive decline associated with stroke, poststroke neuroprotection, cognitive and sensorimotor gating deficits associated with schizophrenia, cognitive deficits associated with bipolar disorder, cognitive impairments associated with depression, acute pain, post-surgical or post-operative pain, chronic pain, inflammation, inflammatory pain, neuropathic pain, smoking cessation, need for new blood vessel growth associated with wound healing, need for new blood vessel growth associated with vascularization of skin grafts, and lack of circulation, arthritis, rheumatoid arthritis, psoriasis, Crohn's disease, ulcerative colitis, pouchitis, inflammatory bowel disease, celiac disease, periodontitis, sarcoidosis, pancreatitis, organ transplant rejection, acute immune disease associated with organ transplantation, chronic immune disease associated with organ transplantation, septic shock, toxic shock syndrome, sepsis syndrome, depression, and rheumatoid spondylitis.

In another embodiment, the pharmaceutical compositions are useful for the treatment and/or prophylaxis of diseases or disorder or condition classified or diagnosed as major or minor neurocognitive disorders, or disorders arising due to neurodegeneration.

The present invention also provide method of administering a compound of formula (I), as defined hereinabove in combination with or as adjunct to medications used in the treatment of attention deficit hyperactivity disorders, schizophrenia, and other cognitive disorders such as Alzheimer's disease, Parkinson's dementia, vascular dementia or dementia associated with Lewy bodies, traumatic brain injury.

The present invention also provide method of administering a compound of formula (I), as defined hereinabove in combination with or as an adjunct to acetylcholinesterase inhibitors, disease modifying drugs or biologics for neurodegenerative disorders, dopaminergic drugs, antidepressants, typical or an atypical antipsychotic.

Accordingly, compound of formula (I) is useful for preventing or treating a disorder mediated by nicotinic acetylcholine receptors. Such compounds can be administered to a subject having such a disorder or susceptible to such disorders in a therapeutically effective amount. The compounds are particularly useful for a method of treating a mammal having a condition where modulation of nicotinic acetylcholine receptor activity is of therapeutic benefit, wherein the method is accomplished by administering a therapeutically effective amount of a compound of formula (I) to a subject having, or susceptible to, such a disorder.

The present invention also provides a pharmaceutical composition, containing the compound of the general formula (I) as defined above, its tautomeric forms, its stereoisomers, its analogs, its prodrugs, its isotopes, its metabolites, its pharmaceutically acceptable salts, its polymorphs, its solvates, its optical isomers, its clathrates and its co-crystals in combination with the usual pharmaceutically employed carriers, diluents and the like, and for use in any of the methods described herein.

The compounds of the invention can be administered in a dose sufficient to treat the disease, condition or disorder. Such doses are known in the art (see, for example, the *Physicians' Desk Reference* (2004)). The compounds can be administered using techniques such as those described in, for example, Wasserman et al., *Cancer,* 36, pp. 1258-1268 (1975) and *Physicians' Desk Reference,* 58th ed., Thomson P D R (2004).

Suitable doses and dosage regimens can be determined by conventional range-finding techniques known to those of ordinary skill in the art. Generally, treatment is initiated with smaller dosages that are less than the optimum dose of the compound of the present invention. Thereafter, the dosage is increased by small increments until the optimum effect under the circumstances is reached. The present method can involve the administration of about 0.1 µg to about 50 mg of at least one compound of the invention per kg body weight of the individual. For a 70 kg patient, dosages of from about 10 µg to about 200 mg of the compound of the invention would be more commonly used, depending on a patient's physiological response.

By way of example and not intending to limit the invention, the dose of the pharmaceutically active agent(s) described herein for methods of treating or preventing a disease or condition as described above can be about 0.001 to about 1 mg/kg body weight of the subject per day, for example, about 0.001 mg, 0.002 mg, 0.005 mg, 0.010 mg, 0.015 mg, 0.020 mg, 0.025 mg, 0.050 mg, 0.075 mg, 0.1 mg, 0.15 mg, 0.2 mg, 0.25 mg, 0.5 mg, 0.75 mg, or 1 mg/kg body weight per day. The dose of the pharmaceutically active agent(s) described herein for the described methods can be about 1 to about 1000 mg/kg body weight of the subject being treated per day, for example, about 1 mg, 2 mg, 5 mg, 10 mg, 15 mg, 0.020 mg, 25 mg, 50 mg, 75 mg, 100 mg, 150 mg, 200 mg, 250 mg, 500 mg, 750 mg, or 1000 mg/kg body weight per day.

In accordance with embodiments, the present invention provides methods of treating, preventing, ameliorating, and/or inhibiting a condition modulated by the nicotinic acetylcholine receptor comprising administering a compound of formula (I) or a salt thereof.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the inventive methods can provide any amount of any level of treatment, prevention, amelioration, or inhibition of the disorder in a mammal. For example, a disorder, including symptoms or conditions thereof, may be reduced by, for example, 100%, 90%, 80%, 70%, 60%, 50%, 40%, 30%, 20%, or 10%. Furthermore, the treatment, prevention, amelioration, or inhibition provided by the inventive method can include treatment, prevention, amelioration, or inhibition of one or more conditions or symptoms of the disorder, e.g., cancer. Also, for purposes herein, "treatment," "prevention," "amelioration," or "inhibition" can encompass delaying the onset of the disorder, or a symptom or condition thereof.

In accordance with the invention, the term subject includes an "animal" which in turn includes a mammal such as, without limitation, the order Rodentia, such as mice, and the order Lagomorpha, such as rabbits. It is preferred that the mammals are from the order Carnivora, including Felines (cats) and Canines (dogs). It is more preferred that the mammals are from the order Artiodactyla, including Bovines (cows) and Swine (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

Following are the abbreviations used and meaning thereof in the specification:
ACh: Acetylcholine.
AD: Alzheimer's disease.
ADC: AIDS dementia complex.
ADHD: attention deficit hyperactivity disorder.
AIDS: Acquired immunodeficiency syndrome.
ARDS: acute respiratory distress syndrome.
DCC: 1,3-dicyclohexylcarbodiimide.
DCM: dichloromethane.
DIPEA: diisopropyl ethyl amine
DLB: dementia with Lewy bodies.
DMF: N,N-dimethylformamide.
EDCI: 1-(3-dimethylaminopropyl)-3-ethylcarbodiimide hydrochloride.
FLIPR: Fluorometric Imaging Plate Reader.
HATU: 2-(1H-7-Azabenzotriazol-1-yl)-1,1,3,3-tetramethyl uronium hexafluorophosphate.
HBSS: Hank's balanced salt solution.
HEPES: 4-(2-hydroxyethyl)piperazine-1-ethanesulfonic acid.
HMGB: high mobility group box.
HOAT: 1-hydroxy-7-azabenzotriazole.
HOBT: hydroxybenzotriazole hydrate.
HPLC: High Performance liquid chromatography.
IL: interleukins.
LDT: laterodorsal tegmental nucleus.
LGIC: ligand-gated ion channels.
MCI: mild cognitive impairment.
NBS: N-bromosuccinimide.
NNRs: Neural nicotinic ACh receptors.
PAM: positive allosteric modulation.
PD: Parkinson's disease.
PDN: post-diabetic neuralgia.
PHN: post-herpetic neuralgia.
PNS: peripheral nervous system.
TBI: traumatic brain injury.
THF: Tetrahydrofuran.
TLC: Thin layer chromatography.
TMS: tetramethylsilane.
TNF-α: tumor necrosis factor alpha.
VTA: ventral tegmental area.
α7 nAChR: nicotinic acetylcholine receptor α7 subunit.

The following examples are provided to further illustrate the present invention and therefore should not be construed in any way to limit the scope of the present invention. All ¹HNMR spectra were determined in the solvents indicated and chemical shifts are reported in δ units downfield from the internal standard tetramethylsilane (TMS) and interproton coupling constants are reported in Hertz (Hz).

EXAMPLE 1

Synthesis of 2'-Methoxy-5'-(3-methyl-5-propionylthiophen-2-yl)-[1,1'-biphenyl]-4-sulfonamide (Compound 1)

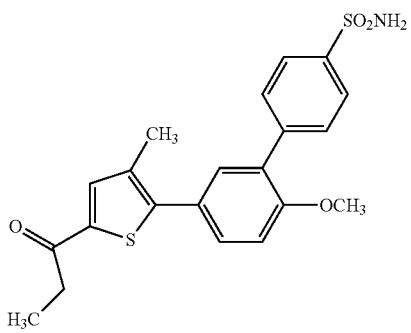 [SMILES: CCC(=O)c1cc(C)c(-c2ccc(OC)c(-c3ccc(S(N)(=O)=O)cc3)c2)s1]

Step 1: Methyl 5-(3-bromo-4-methoxyphenyl)-4-methylthiophene-2-carboxylate (1a)

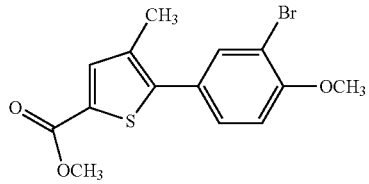 [SMILES: COC(=O)c1cc(C)c(-c2ccc(OC)c(Br)c2)s1]

Liquid bromine (1.8 g, 0.57 ml, 11.43 mmol) was added drop wise to a stirred solution of methyl-5-(4-methoxyphenyl)-4-methylthiophene-2-carboxylate (prepared according to the procedure reported in WO 2007/092751, 2.0 g, 7.62 mmol) in acetic acid (20 ml) at a temperature of about 25° C. The resulting mixture was stirred at the same temperature for 16 hours. The progress of reaction was monitored by TLC. The reaction mixture was poured onto ice water (100 ml). The mixture so obtained was extracted with ethyl acetate (3×100 ml). The separated combined organic layer was washed with 10% aqueous sodium bicarbonate solution (2×50 ml). The organic layer was then dried over anhydrous $Na_2SO_4$. The solvent was evaporated form the organic layer under reduced pressure to obtain a crude product. The crude product was further purified by flash chromatography using 15-25% ethyl acetate in hexanes as an eluent to obtain the title compound (2.35 g, 90%).

MS: m/z 341 (M+1).

¹HNMR (CDCl₃, 400 MHz): δ 7.67 (d, J=2.4 Hz, 1H), 7.61 (s, 1H), 7.39 (dd, J=2.4 Hz, 8.8 Hz, 1H), 6.96 (d, J=8.8 Hz, 1H), 3.95 (s, 3H), 3.89 (s, 3H), 2.30 (s, 3H).

The compounds listed below were prepared by procedure similar to the one described above for compound '1a' with appropriate variations in reactants, reaction conditions and quantities of reagents.

2a. Methyl 5-(3-bromo-4-chlorophenyl)-4-methylthiophene-2-carboxylate
3a. Methyl 5-(3-bromophenyl)-4-methylthiophene-2-carboxylate
4a. Methyl 5-(3-bromo-4-(dimethylamino)phenyl)-4-methylthiophene-2-carboxylate Step 2: Ethyl 5-(6-methoxy-4'-sulfamoyl-[1,1'-biphenyl]-3-yl)-4-methylthiophene-2-carboxylate (2b)

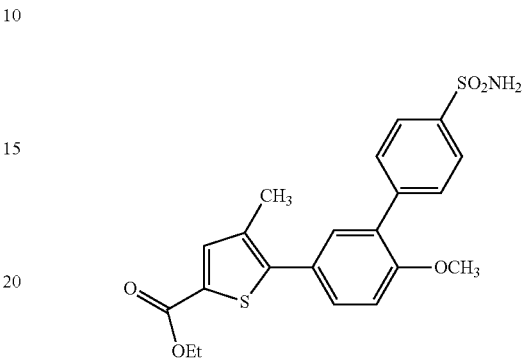

4-aminosulfonylbenzene boronic acid (prepared according to the procedure given in EP 1 012 142, 1.16 g, 5.8 mmol) and potassium carbonate (1.45 g, 10.55 mmol) were added to the solution of methyl 5-(3-bromo-4-methoxyphenyl)-4-methylthiophene-2-carboxylate (1a, 1.8 g, 5.27 mmol) in a mixture of toluene:ethanol (9:27 ml) at a temperature of about 25° C. in a tube under nitrogen atmosphere for 15 minutes. Tetrakis(triphenylphosphine)palladium(0) (0.3 g, 0.26 mmol) was added to the reaction mixture under nitrogen and the tube was sealed. Reaction mixture was heated at about 90-95° C. for 16 hr under stirring. Completion of the reaction was monitored by TLC. The reaction mixture was then cooled to 25° C. and filtered through celite. The celite cake was washed with 10% methanol in dichloromethane. The combined filtrate was then concentrated under reduced pressure to obtain a crude product. The crude product so obtained was purified by flash chromatography using 4% methanol in dichloromethane as an eluent to obtain the title compound 1b (1.5 g, 68%).

MS: m/z 432 (M+1).

¹HNMR (DMSO-d6, 400 MHz): δ 7.86 (d, J=8.4 Hz, 2H), 7.71 (d, J=8.4 Hz, 2H), 7.68 (s, 1H), 7.57 (dd, J=2.4 Hz, 8.8 Hz, 1H), 7.45 (d, J=2.4 Hz, 1H), 7.4 (bs-exchange with D₂O, 2H), 7.27 (d, J=8.8 Hz, 1H), 4.27 (q, J=7.2 Hz, 2H), 3.84 (s, 3H), 2.31 (s, 3H), 1.28 (t, J=7.2 Hz, 3H).

Note: Due to trans-esterification, it is fully converted into corresponding ethyl ester. However, mixture of ethyl ester and methyl ester is also obtained during some experiments due to partial conversion methyl ester into corresponding ethyl ester.

The compounds given below were prepared by procedure similar to the one described above for compound '1b' with appropriate variations in reactants, reaction conditions and quantities of reagents.

2b. Ethyl 5-(6-chloro-4'-sulfamoyl-[1,1'-biphenyl]-3-yl)-4-methylthiophene-2-carboxylate
MS: m/z 436 (M+1).
3b. Ethyl 4-methyl-5-(4'-sulfamoyl-[1,1'-biphenyl]-3-yl)thiophene-2-carboxylate
MS: m/z 402 (M+1).
4b. Ethyl 5-(6-(dimethylamino)-4'-sulfamoyl-[1,1'-biphenyl]-3-yl)-4-methylthiophene-2-carboxylate
MS: m/z 445 (M+1).

Step 3: 5-(6-methoxy-4'-sulfamoyl-[1,1'-biphenyl]-3-yl)-4-methylthiophene-2-carboxylic acid (1c)

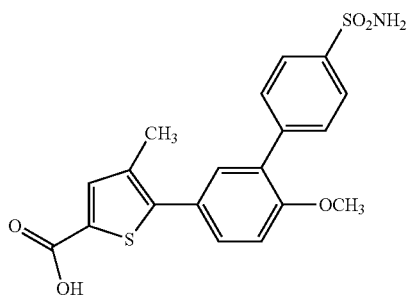 [SMILES: CCOC(=O)c1cc(C)c(-c2ccc(OC)c(-c3ccc(S(N)(=O)=O)cc3)c2)s1]

Ethyl 5-(6-methoxy-4'-sulfamoyl-[1,1'-biphenyl]-3-yl-4-methylthiophene-2-carboxylate (1b, 1.4 g, 3.24 mmol) was suspended in ethanol (21 ml), to this was added 1N solution of NaOH (16 ml) at 25° C. The reaction mixture was heated at about 85° C. under stirring for 30-40 minutes. The progress of the reaction was monitored by TLC. Reaction mixture was concentrated at reduced pressure. Residue was diluted with water (10 ml). To the resulting diluted mixture was added aqueous 2N HCl to bring the pH of the mixture to about 1 at 0° C. The solid obtained was filtered and dried to obtain the title compound (1.3 g, 99.3%).

MS: m/z 404 (M+1).

$^1$HNMR (DMSO-$d_6$, 400 MHz): δ 13.01 (bs-exchange with $D_2O$, 1H), 7.86 (d, J=8.4 Hz, 2H), 7.72 (d, J=8.4 Hz, 2H), 7.61 (s, 1H), 7.56 (dd, J=2.4 Hz, 8.8 Hz, 1H), 7.44 (d, J=2.4 Hz, 1H), 7.4 (bs-exchange with $D_2O$, 2H), 7.25 (d, J=8.8 Hz, 1H), 3.84 (s, 3H), 2.30 (s, 3H).

The compounds given below were prepared by following a procedure similar to the one described above for compound '1c' with appropriate variations of reactants, reaction conditions and quantities of reagents.

2c. 5-(6-chloro-4'-sulfamoyl-[1,1'-biphenyl]-3-yl)-4-methylthiophene-2-carboxylic acid
MS: m/z 408 (M+1).

3c. 4-methyl-5-(4'-sulfamoyl-[1,1'-biphenyl]-3-yl)thiophene-2-carboxylic acid
MS: m/z 374 (M+1).

4c. 5-(6-(dimethylamino)-4'-sulfamoyl-[1,1'-biphenyl]-3-yl)-4-methylthiophene-2-carboxylic acid
MS: m/z 417 (M+1).

Step 4: 5-(4'-(N-((dimethylamino)methylene)sulfamoyl)-6-methoxy-[1,1'-biphenyl]-3-yl)-N-methoxy-N,4-dimethylthiophene-2-carboxamide (1d)

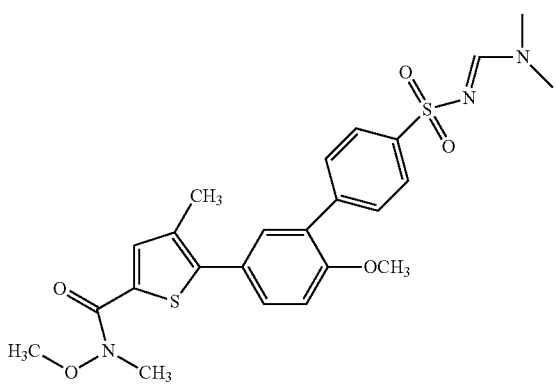

Oxalyl chloride (0.87 g, 0.58 ml, 6.94 mmol) was added drop wise to a solution of 5-(6-methoxy-4'-sulfamoyl-[1,1'-biphenyl]-3-yl)-4-methylthiophene-2-carboxylic acid (1c, 1.4 g, 3.47 mmol) in dichloromethane (28 ml) and DMF (0.53 ml, 6.94 mmol) at 0° C. The reaction mixture was then allowed to come to room temperature and stirred for 1.5 hr under nitrogen atmosphere. The progress of the reaction was monitored by TLC. The reaction mixture was then concentrated under reduced pressure and used directly for further reaction. Residue obtained after concentration was dissolved in dry dichloromethane (20 ml) and to this was added triethylamine (2.1 g, 2.89 ml, 20.8 mmol) followed by the addition of N,O-dimethylhydroxylamine hydrochloride (1.34 g, 13.88 mmol) under stirring. The reaction mixture was stirred at room temperature for 2 hours. The progress of the reaction was monitored by TLC. The reaction mixture was then diluted with dichloromethane (100 ml). The mixture obtained was washed with water (2×20 ml), followed by washing with brine (1×20 ml). The separated organic layer was dried over anhydrous sodium sulphate, and concentrated under reduced pressure to obtain a crude product. The crude product was further purified by column chromatography over silica gel using 80% ethyl acetate in hexane as an eluent to obtain the title compound (1.1 g, 63.2%).

MS: m/z 502 (M+1).

$^1$HNMR (CDCl$_3$, 400 MHz): δ 8.17 (s, 1H), 7.94 (d, J=8.4 Hz, 2H), 7.78 (s, 1H), 7.66 (d, J=8.4 Hz, 2H), 7.48 (dd, J=2.4 Hz, 8.8 Hz, 1H), 7.42 (d, J=2.4 Hz, 1H), 7.06 (d, J=8.8 Hz, 1H), 3.85 (s, 3H), 3.79 (s, 3H), 3.37 (s, 3H), 3.13 (s, 3H), 3.05 (s, 3H), 2.32 (s, 3H).

The compounds given below were prepared by following a procedure similar to the one described above for compound '1d' with appropriate variations of reactants, reaction conditions and quantities of reagents.

2d. 5-(6-chloro-4'-(N-((dimethylamino)methylene)sulfamoyl)-[1,1'-biphenyl]-3-yl)-N-methoxy-N,4-dimethylthiophene-2-carboxamide
MS: m/z 506 (M+1).

3d. 5-(4'-(N-((dimethylamino)methylene)sulfamoyl)-[1,1'-biphenyl]-3-yl)-N-methoxy-N,4-dimethylthiophene-2-carboxamide
MS: m/z 472 (M+1).

4d. 5-(6-(dimethylamino)-4'-(N-((dimethylamino)methylene)sulfamoyl)-[1,1'-biphenyl]-3-yl)-N-methoxy-N,4-dimethylthiophene-2-carboxamide
MS: m/z 515 (M+1).

Step 5: 2'-Methoxy-5'-(3-methyl-5-propionylthiophen-2-yl)-[1,1'-biphenyl]-4-sulfonamide (Compound 1)

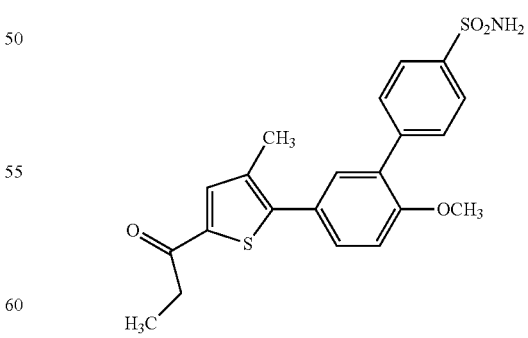

Grignard reagent (ethyl magnesium bromide, 1.32 g, 9.9 ml, 9.97 mmol) was added drop wise to a stirred solution of 5-(4'-(N-((dimethylamino)methylene)sulfamoyl)-6-methoxy-[1,1'-biphenyl]-3-yl)-N-methoxy-N,4-dimethylthiophene-2-carboxamide (1d, 1.0 g, 1.99 mmol) in anhydrous THF (20 ml) at 25° C. The reaction mixture was heated at 80-85° C. for 1 hour. The progress of the reaction was monitored by TLC. The reaction mixture was cooled to 0° C. The cooled reaction mixture was then quenched by adding a saturated solution of ammonium chloride (10 ml). The mixture was then extracted with ethyl acetate (3×60 ml). The combined organic layer was dried over anhydrous $Na_2SO_4$. The solvent was evaporated from the dried organic layer under reduced pressure to obtain a crude product. The crude product so obtained was purified by flash chromatography using 30-40% ethyl acetate in hexane as an eluent to obtain the title compound. The compound was re-purified by dissolving 0.68 g of the compound in ethyl acetate (5 ml) and precipitating it by slow addition of diisopropyl ether. (0.180 g, 21.7%).

MS: m/z 416 (M+1).

$^1$HNMR (DMSO-$d_6$, 400 MHz): δ 7.86 (d, J=8.4 Hz, 2H), 7.83 (s, 1H), 7.71 (d, J=8.4 Hz, 2H), 7.58 (dd, J=2.4 Hz, 8.8 Hz, 1H), 7.45 (d, J=2.4 Hz, 1H), 7.41 (bs, exchanges with $D_2O$, 2H), 7.27 (d, J=8.8 Hz, 1H), 3.84 (s, 3H), 2.95 (q, J=7.2 Hz, 2H), 2.32 (s, 3H), 1.09 (t, J=7.2 Hz, 3H).

The compounds given below were prepared by following a procedure similar to the one described above for compound '1' with appropriate variations of reactants, reaction conditions and quantities of reagents.

Compound 2: 2'-chloro-5'-(3-methyl-5-propionylthiophen-2-yl)-[1,1'-biphenyl]-4-sulfonamide MS: m/z 420 (M+1).

$^1$HNMR (DMSO-$d_6$, 400 MHz): δ 7.92 (d, J=8.4 Hz, 2H), 7.86 (s, 1H), 7.70-7.74 (m, 3H), 7.62 (dd, J=2.4, 8.4 Hz, 1H), 7.56 (d, J=2.4 Hz, 1H), 7.47 (bs-exchanges with $D_2O$, 2H), 2.95 (q, J=7.6 Hz, 2H), 2.34 (s, 3H), 1.09 (t, J=7.6 Hz, 3H).

Compound 3: 3'-(3-methyl-5-propionylthiophen-2-yl)-[1,1'-biphenyl]-4-sulfonamide MS: m/z 386 (M+1).

$^1$HNMR (CDCl$_3$, 400 MHz): δ 8.01 (d, J=8.4 Hz, 2H), 7.73 (d, J=8.4 Hz, 2H), 7.68 (s, 1H), 7.48-7.62 (m, 4H), 4.87 (bs-exchanges with $D_2O$, 2H), 2.93 (q, J=7.2 Hz, 2H), 2.37 (s, 3H), 1.23 (t, J=7.2 Hz, 3H).

Compound 4: 2'-(dimethylamino)-5'-(3-methyl-5-propionylthiophen-2-yl)-[1,1'-biphenyl]-4-sulfonamide MS: m/z 429 (M+1).

$^1$HNMR (CDCl$_3$, 400 MHz): δ 7.99 (d, J=8.4 Hz, 2H), 7.76 (d, J=8.4 Hz, 2H), 7.53 (s, 1H), 7.70-7.45 (dd, J=2.0, 8.4 Hz, 1H), 7.32 (d, J=2.4 Hz, 1H), 7.11 (d, J=8.4 Hz, 1H), 4.91 (bs-exchanges with $D_2O$, 2H), 2.94 (q, J=7.2 Hz, 2H), 2.61 (s, 6H), 2.36 (s, 3H), 1.25 (t, J=7.2 Hz, 3H).

EXAMPLE 2

Preparation of 2'-methoxy-5'-(4-methyl-2-(piperidine-1-carbonyl)thiazol-5-yl)-[1,1'-biphenyl]-4-sulfonamide (Compound 5)

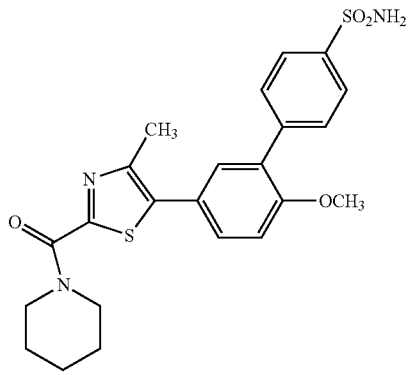 [SMILES: COc1ccc(-c2sc(C(=O)N3CCCCC3)nc2C)cc1-c1ccc(S(N)(=O)=O)cc1]

Step 1: (5-(4-methoxyphenyl)-4-methylthiazol-2-yl)(piperidin-1-yl)methanone (5a)

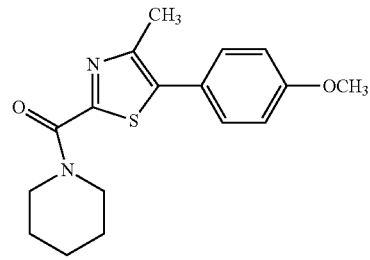 [SMILES: COc1ccc(-c2sc(C(=O)N3CCCCC3)nc2C)cc1]

Piperidine (1.84 g, 21.63 mmol) was added to a stirred solution of ethyl 5-(4-methoxyphenyl)-4-methylthiazole-2-carboxylate (prepared according to the procedure reported in WO 2006/089076, 0.6 g, 2.16 mmol) in a ethanol (10 ml) in a tube at 25° C. under nitrogen atmosphere. The tube was agitated for about 15 minutes under nitrogen and was sealed. The reaction mixture was heated at 90-95° C. for 15 hr with stirring. The progress of the reaction was monitored by TLC. The reaction mixture was then cooled to 25° C. and was concentrated under reduced pressure. The residue obtained was dissolved in ethyl acetate (50 ml). The mixture was washed with saturated sodium bicarbonate solution (20 ml). The separated organic layer was concentrated under reduced pressure to obtain a crude product, which was then purified by flash column chromatography using 40% ethyl acetate in hexanes as an eluent to obtain the title compound (0.50 g, 73.0%).

MS: m/z 317 (M+1).

$^1$HNMR (DMSO-$d_6$, 400 MHz): δ 7.47 (d, J=8.8 Hz, 2H), 7.05 (d, J=8.8 Hz, 2H), 4.21-4.24 (m, 2H), 3.79 (s, 3H), 3.59-3.62 (m, 2H), 2.45 (s, 3H), 1.57-1.65 (m, 6H).

The compound given below was prepared by following a procedure similar to the one described above for compound '5a' with appropriate variations of reactants, reaction conditions and quantities of reagents.

6a. (5-(4-methoxyphenyl)-4-methylthiazol-2-yl)(pyrrolidin-1-yl)methanone

MS: m/z 303 (M+1).

7a. (5-(4-chlorophenyl)-4-methylthiazol-2-yl)(pyrrolidin-1-yl)methanone

Step 2: (5-(3-bromo-4-methoxyphenyl)-4-methylthiazol-2-yl)(piperidin-1-yl)methanone (5b)

Liquid bromine (0.30 g, 0.097 ml, 1.89 mmol) was added drop wise to a stirred solution (5-(4-methoxyphenyl)-4-methylthiazol-2-yl)(piperidin-1-yl)methanone (5a, 0.5 g, 1.58 mmol) in acetic acid (6 ml) at 25° C. The resulting mixture was stirred at 25° C. for 3 hrs. The progress of the reaction was monitored by TLC. The reaction mixture was then concentrated under reduced pressure. The residue obtained after concentration was dissolved in ethyl acetate (50 ml). The mixture was then washed with saturated sodium bicarbonate solution (20 ml). The separated organic layer was concentrated under reduced pressure to obtain a crude product, which was then purified by flash column chromatography using 30% ethyl acetate in hexanes as an eluent to obtain the title compound 5b (0.54 g, 86.0%).

MS: m/z 396 (M+1).

$^1$HNMR (DMSO-$d_6$, 400 MHz): δ 7.74 (d, J=2.0 Hz, 1H), 7.53 (dd, J=8.4, 2.0 Hz, 1H), 7.22 (d, J=8.4 Hz, 1H), 4.20-4.22 (m, 2H), 3.90 (s, 3H), 3.59-3.61 (m, 2H), 2.44 (s, 3H), 1.52-1.65 (m, 6H).

The compounds given below were prepared by following a procedure similar to the one described above for compound '5b' with appropriate variations of reactants, reaction conditions and quantities of reagents.

6b. (5-(3-bromo-4-methoxyphenyl)-4-methylthiazol-2-yl)(pyrrolidin-1-yl)methanone MS: m/z 382 (M+1).

7b. (5-(3-bromo-4-chlorophenyl)-4-methylthiazol-2-yl)(pyrrolidin-1-yl)methanone

MS: m/z 386 (M+1).

Step 3: 2'-methoxy-5'-(4-methyl-2-(piperidine-1-carbonyl)thiazol-5-yl)-[1,1'-biphenyl]-4-sulfonamide (Compound 5)

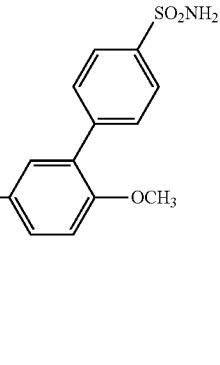

4-aminosulfonylbenzene boronic acid (0.42 g, 2.12 mmol) and potassium carbonate (0.73 g, 5.31 mmol) were added to a solution of (5-(3-bromo-4-methoxyphenyl)-4-methylthiazol-2-yl)(piperidin-1-yl)methanone (5b, 0.70 g, 1.77 mmol) in a mixture of toluene:ethanol (5 ml:15 ml) in a tube at about 25° C. under nitrogen atmosphere. The reaction mixture was agitated under nitrogen atmosphere for 15 minutes, to it was then added tetrakis(triphenylphosphine) palladium(0) (0.10 g, 0.089 mmol) under nitrogen and the tube was sealed. The reaction mixture was heated at 90-95° C. for 18 hr with stirring. The progress of the reaction was monitored by TLC. The reaction mixture was then cooled to 25° C. and filtered through celite. The celite cake was washed with mixture of 10% methanol in dichloromethane (2×20 ml). The combined filtrate was concentrated under reduced pressure to obtain a crude product, which was then purified by flash column chromatography using 40% ethyl acetate in hexanes as an eluent to obtain the title compound 5 (0.20 g, 23.9%).

MS: m/z 472 (M+1).

$^1$HNMR (DMSO-$d_6$, 400 MHz): δ 7.85 (d, J=8.4 Hz, 2H), 7.70 (d, J=8.4 Hz, 2H), 7.58 (dd, J=8.8, 2.4 Hz, 1H), 7.46 (d, J=2.4 Hz, 1H), 7.33 (bs-exchanges with $D_2O$, 2H), 7.27 (d, J=8.8 Hz, 1H), 4.21-4.23 (m, 2H), 3.84 (s, 3H), 3.59-3.61 (m, 2H), 2.47 (s, 3H), 1.57-1.65 (m, 6H).

The compounds given below were prepared by following a procedure similar to the one described above for compound '5' with appropriate variations of reactants, reaction conditions and quantities of reagents.

Compound 6: 2'-methoxy-5'-(4-methyl-2-(pyrrolidine-1-carbonyl)thiazol-5-yl)-[1,1'-biphenyl]-4-sulfonamide MS: m/z 458 (M+1).

$^1$HNMR (CDCl$_3$, 400 MHz): δ 7.98 (d, J=8.8 Hz, 2H), 7.70 (d, J=8.8 Hz, 2H), 7.49 (dd, J=8.8, 2.4 Hz, 1H), 7.41 (d, J=2.4 Hz, 1H), 7.08 (d, J=8.8 Hz, 1H), 4.86 (bs-exchanges with $D_2O$, 2H), 4.12 (t, J=6.4 Hz, 2H), 3.88 (s, 3H), 3.69 (t, J=6.4 Hz, 2H), 2.54 (s, 3H), 2.01 (quintet, J=6.0 Hz, 2H), 1.97 (quintet, J=6.0 Hz, 2H).

Compound 7: 2'-chloro-5'-(4-methyl-2-(pyrrolidine-1-carbonyl)thiazol-5-yl)-[1,1'-biphenyl]-4-sulfonamide MS: m/z 462 (M+1).

$^1$HNMR (CDCl$_3$, 400 MHz): δ 8.04 (d, J=8.4 Hz, 2H), 7.64 (d, J=8.4 Hz, 2H), 7.58 (d, J=8.4 Hz, 1H), 7.45 (dd, J=8.4, 2.0 Hz, 1H), 7.41 (d, J=2.0 Hz, 1H), 5.00 (bs-exchanges with $D_2O$, 2H), 4.13 (t, J=6.8 Hz, 2H), 3.69 (t, J=6.8 Hz, 2H), 2.54 (s, 3H), 2.01 (quintet, J=6.4 Hz, 2H), 1.94 (quintet, J=6.4 Hz, 2H).

EXAMPLE 3

Preparation of 2'-methoxy-5'-(4-methyl-2-propionylthiazol-5-yl)-[1,1'-biphenyl]-4-sulfonamide (Compound 8)

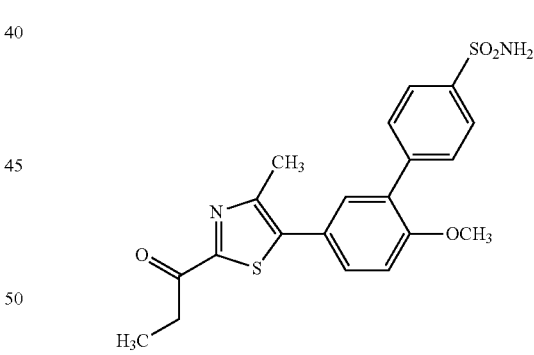

Step 1: Ethyl 5-(3-bromo-4-methoxyphenyl)-4-methylthiazole-2-carboxylate (8a)

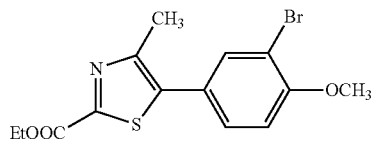 [SMILES: CCOC(=O)c1nc(C)c(-c2ccc(OC)c(Br)c2)s1]

Liquid bromine (1.04 g, 0.36 ml, 6.49 mmol) was added to a stirred solution of ethyl 5-(4-methoxyphenyl)-4-methylthiazole-2-carboxylate (prepared according to the procedure reported in WO 2006/089076, 1.5 g, 5.41 mmol) in acetic acid (15 ml) at 25° C. The resulting reaction mixture was then stirred at 25° C. for 3 hours. The progress of the reaction was monitored by TLC. The reaction mixture was then concentrated under reduced pressure. The residue obtained after concentration was dissolved in ethyl acetate (100 ml). The mixture obtained was washed with saturated sodium bicarbonate solution (30 ml). The separated organic layer was concentrated under reduced pressure to obtain a crude product, which was then purified by flash column chromatography using 30% ethyl acetate in hexanes as an eluent to obtain the title compound 8a (1.70 g, 88.5%).

MS: m/z 357 (M+1).

¹HNMR (CDCl₃, 400 MHz): δ 7.66 (d, J=2.4 Hz, 1H), 7.39 (dd, J=8.4, 2.4 Hz, 1H), 6.98 (d, J=8.4 Hz, 1H), 4.50 (q, J=7.2 Hz, 2H), 3.96 (s, 3H), 2.57 (s, 3H), 1.45 (t, J=7.2 Hz, 3H).

Step 2: 5-(6-methoxy-4'-sulfamoyl-[1,1'-biphenyl]-3-yl)-4-methylthiazole-2-carboxylic acid (8b)

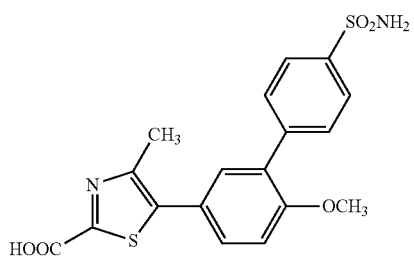 [SMILES: COc1ccc(-c2sc(C(=O)O)nc2C)cc1-c1ccc(S(N)(=O)=O)cc1]

4-aminosulfonylbenzene boronic acid (1.15 g, 5.73 mmol) and potassium carbonate (1.97 g, 14.31 mmol) were added to a solution of ethyl 5-(3-bromo-4-methoxyphenyl)-4-methylthiazole-2-carboxylate (Step 1, 1.70 g, 4.77 mmol) in a mixture of toluene:ethanol (15 ml:40 ml) in a tube at 25° C. Nitrogen gas was bubbled through reaction mixture for 15 minutes and to it was added tetrakis(triphenylphosphine)palladium (0) (0.28 g, 0.24 mmol) under nitrogen and the tube was sealed. The reaction mixture was heated at 90-95° C. for 18 hr with stirring. The progress of the reaction was monitored by TLC. The reaction mixture was then cooled to 25° C. and filtered through celite. The celite cake was then washed with 10% methanol in dichloromethane (3×30 ml). The filtrate was dried over sodium sulphate and was concentrated under reduced pressure to obtain the title compound 8b (1.70 g, 88.08%).

MS: m/z 405 (M+1).

¹HNMR (DMSO-d₆, 400 MHz): δ 11.33 (bs-exchanges with D₂O, 1H), 7.86 (d, J=8.4 Hz, 2H), 7.70 (d, J=8.4 Hz, 2H), 7.51 (dd, J=8.4, 2.0 Hz, 1H), 7.39-7.41 (m, 3H), 7.24 (d, J=8.4 Hz, 1H), 3.83 (s, 3H), 2.43 (s, 3H).

Step 3: N-methoxy-5-(6-methoxy-4'-sulfamoyl-[1,1'-biphenyl]-3-yl)-N,4-dimethylthiazole-2-carboxamide (8c)

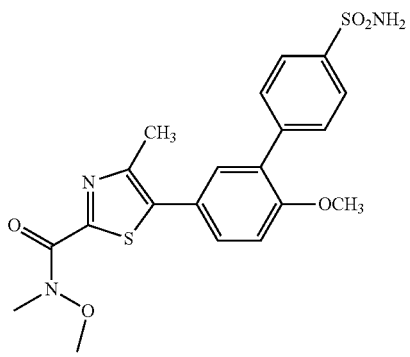 [SMILES: COc1ccc(-c2sc(C(=O)N(C)OC)nc2C)cc1-c1ccc(S(N)(=O)=O)cc1]

HOBT (0.62 g, 4.62 mmol) was added to a solution of 5-(6-methoxy-4'-sulfamoyl-[1,1'-biphenyl]-3-yl)-4-methylthiazole-2-carboxylic acid (8b, 1.70 g, 4.20 mmol) in DMF (15 ml) at room temperature under stirring. N,O-dimethylhydroxylamine hydrochloride (0.82 g, 8.40 mmol) was then added to the reaction mixture. The reaction mixture was cooled to 0° C. and to this were added EDC (1.20 g, 6.31 mmol) and triethylamine (1.69 g, 2.34 ml, 16.80 mmol). The reaction mixture was stirred at room temperature for 15 hours. The progress of the reaction was monitored by TLC. The reaction mixture was then concentrated under reduced pressure. The residue so obtained was mixed with ethyl acetate (100 ml). The mixture obtained was washed with saturated sodium bicarbonate solution (20 ml) followed by washing with brine (20 ml). The separated organic layer was dried over anhydrous sodium sulphate. The dried organic layer was then concentrated under reduced pressure to obtain a crude product. The crude product was then purified by column chromatography using 50% ethyl acetate in hexanes as an eluent to obtain the title compound 8c (0.70 g, 37.23%).

MS: m/z 448 (M+1).

¹HNMR (DMSO-d₆, 400 MHz): δ 7.87 (d, J=8.4 Hz, 2H), 7.72 (d, J=8.8 Hz, 2H), 7.60 (dd, J=8.4, 2.4 Hz, 1H), 7.48 (d, J=2.4 Hz, 1H), 7.40 (bs-exchanges with D₂O, 2H), 7.29 (d, J=8.4 Hz, 1H), 3.85 (s, 3H), 3.80 (s, 3H), 3.49 (s, 3H), 2.51 (s, 3H).

Step 4: 5-(4'-(N-((dimethylamino)methylene)sulfamoyl)-6-methoxy-[1,1'-biphenyl]-3-yl)-N-methoxy-N,4-dimethylthiazole-2-carboxamide (8d)

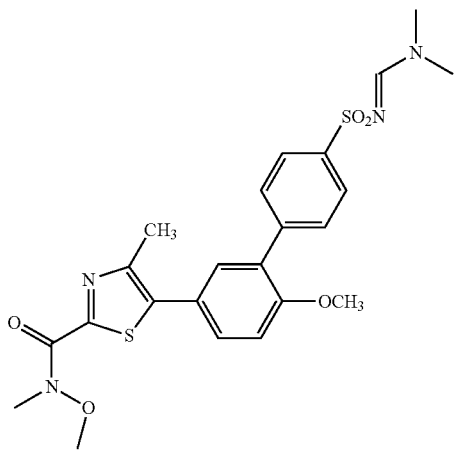

DMF (0.7 ml) and DMF acetal (0.22 g, 0.25 ml, 1.88 mmol) were added subsequently to a solution of N-methoxy-5-(6-methoxy-4'-sulfamoyl-[1,1'-biphenyl]-3-yl)-N,4-dimethylthiazole-2-carboxamide (8c, 0.70 g, 1.56 mmol) in ethyl acetate (12 ml) at room temperature. The reaction mixture was then stirred at room temperature for 15 hr under nitrogen atmosphere. The progress of the reaction was monitored by TLC. The solid obtained was filtered and washed with ether (10 ml) to obtain the title compound 8d (0.60 g, 76.33%).

MS: m/z 503 (M+1).

$^1$HNMR (DMSO-$d_6$, 400 MHz): δ 8.26 (s, 1H), 7.81 (d, J=8.4 Hz, 2H), 7.67 (d, J=8.4 Hz, 2H), 7.60 (dd, J=8.4, 2.4 Hz, 1H), 7.48 (d, J=2.4 Hz, 1H), 7.28 (d, J=8.4 Hz, 1H), 3.84 (s, 3H), 3.80 (s, 3H), 3.48 (s, 3H), 3.16 (s, 3H), 2.93 (s, 3H), 2.51 (s, 3H).

Step 5: 2'-methoxy-5'-(4-methyl-2-propionylthiazol-5-yl)-[1,1'-biphenyl]-4-sulfonamide (Compound 8)

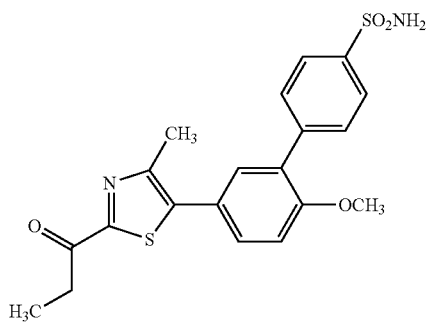 [SMILES: CCC(=O)c1nc(C)c(-c2ccc(OC)c(-c3ccc(S(N)(=O)=O)cc3)c2)s1]

Ethyl magnesium bromide (0.4 g, 2.98 ml, 2.98 mmol) was added drop wise to a solution of 5-(4'-(N-((dimethylamino) methylene)sulfamoyl)-6-methoxy-[1,1'-biphenyl]-3-yl)-N-methoxy-N,4-dimethylthiazole-2-carboxamide (8d, 0.3 g, 0.56 mmol) in anhydrous THF (10 ml) under stirring at 25° C. The reaction mixture was then heated at 70-75° C. for 1 hour. The progress of the reaction was monitored by TLC. The reaction mixture was cooled to 0° C. and quenched by adding a saturated solution of ammonium chloride (10 ml). The mixture was then extracted with ethyl acetate (3×20 ml). The combined organic layer was dried over anhydrous Na$_2$SO$_4$. The solvent was evaporated from the dried organic layer under reduced pressure to obtain a crude product. The crude product was then purified by column chromatography using 30-35% ethyl acetate in hexane as an eluent to obtain the title compound 8 (0.07 g, 28.11%).

MS: m/z 417 (M+1).

$^1$HNMR (DMSO-$d_6$, 400 MHz): δ 7.86 (d, J=8.4 Hz, 2H), 7.71 (d, J=8.4 Hz, 2H), 7.62 (dd, J=8.4, 2.0 Hz, 1H), 7.49 (d, J=2.0 Hz, 1H), 7.40 (bs-exchanges with D$_2$O, 2H), 7.29 (d, J=8.4 Hz, 1H), 3.85 (s, 3H), 3.11 (q, J=7.2 Hz, 2H), 2.54 (s, 3H), 1.12 (t, J=7.2 Hz, 3H).

EXAMPLE 4

Preparation of 5'-(3,4-dimethyl-5-propionylthiophen-2-yl)-2'-methoxy-[1,1'-biphenyl]-4-sulfonamide (Compound 9)

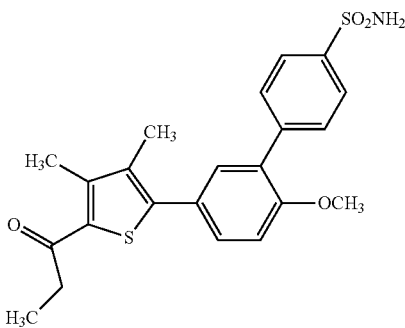 [SMILES: CCC(=O)c1sc(-c2ccc(OC)c(-c3ccc(S(N)(=O)=O)cc3)c2)c(C)c1C]

Step 1: Methyl 3,4-dimethylthiophene-2-carboxylate (9a)

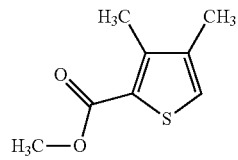

Methyl boronic acid (0.94 g, 16.02 mmol), potassium phosphate (6.8 g, 32.04 mmol) and BINAP (1.33 g, 2.14 mmol) were added to a solution of methyl 3-bromo-4-methylthiophene-2-carboxylate (Prepared according to the procedure reported in Bioorganic Med. Chem. Lett., 2007, 15, 5, 2127-2146, 2.5 g, 10.68 mmol) in a toluene (60 ml) in a tube at 25° C. Nitrogen gas was bubbled through reaction mixture for 15 minutes. Palladium acetate (0.24 g, 1.07 mmol) was added to the reaction mixture under nitrogen and the tube was sealed. The reaction mixture was heated at 95-100° C. for 20 hr under stirring. The progress of the reaction was monitored by TLC. The reaction mixture was cooled to 25° C. and filtered through celite. The celite cake was washed with ethyl acetate (100 ml). The combined filtrate was concentrated under reduced pressure to obtain residue, which was dissolved in ethyl acetate (150 ml) and washed with water (2×30 ml). The separated organic layer was dried over sodium sulphate and concentrated under reduced pressure to obtain a crude product, which was purified by column chromatography using 5% ethyl acetate in hexanes as an eluent to obtain the title compound 9a (1.32 g, 73%).

$^1$HNMR (CDCl$_3$, 400 MHz): δ 7.07 (s, 1H), 3.84 (s, 3H), 2.45 (s, 3H), 2.16 (s, 3H).

Step 2: Methyl 5-bromo-3,4-dimethylthiophene-2-carboxylate (9b)

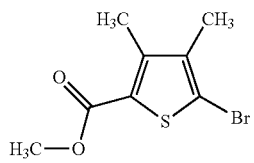

Liquid bromine (1.88 g, 0.6 ml, 11.76 mmol) was added to a stirred solution of methyl 3,4-dimethylthiophene-2-carboxylate (9a, 1.0 g, 5.88 mmol) in DCM (30 ml) at 0° C. The reaction mixture was stirred at 25° C. for 3 hrs. The progress of the reaction was monitored by TLC. The reaction mixture was then concentrated under reduced pressure. The residue obtained after concentration was dissolved in DCM (100 ml). The resulting mixture was washed with water (2×30 ml). The separated organic layer was dried over Na$_2$SO$_4$ and concentrated under reduced pressure to obtain a crude product. The crude product was then purified by column chromatography using 5% ethyl acetate in hexanes as an eluent to obtain the title compound 9b (0.81 g, 58.0%).

$^1$HNMR (CDCl$_3$, 400 MHz): 3.83 (s, 3H), 2.48 (s, 3H), 2.11 (s, 3H).

Step 3: Methyl 5-(4-methoxyphenyl)-3,4-dimethylthiophene-2-carboxylate (9c)

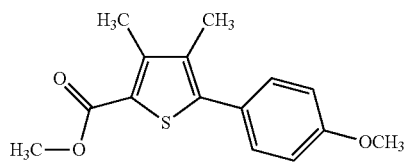 [SMILES: COC(=O)c1sc(-c2ccc(OC)cc2)c(C)c1C]

(4-methoxyphenyl)boronic acid (0.56 g, 3.70 mmol) and potassium carbonate (1.40 g, 10.11 mmol) were added to a solution of methyl 5-bromo-3,4-dimethylthiophene-2-carboxylate (9b, 0.8 g, 3.37 mmol) in a mixture of toluene:ethanol (10:30 ml) in a tube at 25° C. Nitrogen gas was bubbled through reaction mixture for 15 minutes. Tetrakis(triphenylphosphine)(0)palladium (0.19 g, 0.17 mmol) was added to the reaction mixture under nitrogen and the tube was sealed. The reaction mixture was heated at 95-100° C. for 2 hr under stirring. The progress of the reaction was monitored by TLC. The reaction mixture was then cooled to 25° C. and was filtered through celite. The celite cake was washed with ethyl acetate (30 ml). The combined filtrate was concentrated under reduced pressure to obtain a crude product. The resulting crude product was further purified by column chromatography using 5% ethyl acetate in hexanes as an eluent to obtain the title compound 9c (0.84 g, 90%).

MS: m/z 277 (M+1).

$^1$HNMR (CDCl$_3$, 400 MHz): δ 7.36 (d, J=8.8 Hz, 2H), 7.14 (d, J=8.8 Hz, 2H), 3.86 (s, 3H), 3.84 (s, 3H), 2.50 (s, 3H), 2.15 (s, 3H).

Step 4: Methyl 5-(3-bromo-4-methoxyphenyl)-3,4-dimethylthiophene-2-carboxylate (9d)

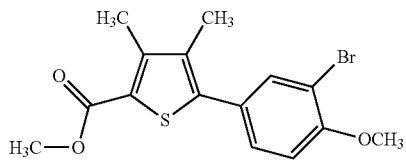 [SMILES: COC(=O)c1sc(-c2ccc(OC)c(Br)c2)c(C)c1C]

Liquid bromine (0.58 g, 0.19 ml, 3.60 mmol) was added to a solution of methyl 5-(4-methoxyphenyl)-3,4-dimethylthiophene-2-carboxylate (step-3, 0.83 g, 3.00 mmol) in acetic acid (20 ml) under stirring at 25° C. The reaction mixture was then stirred at 25° C. for 3 hrs. The progress of the reaction was monitored by TLC. The reaction mixture was concentrated under reduced pressure. The residue was dissolved in ethyl acetate (100 ml). The resulting mixture was washed with saturated sodium bicarbonate solution (30 ml). The separated organic layer was concentrated under reduced pressure to obtain a crude product. The crude product obtained was purified by flash column chromatography using 5% ethyl acetate in hexanes as an eluent to obtain the title compound 9d (0.91 g, 83.0%).

MS: m/z 356 (M+1).

$^1$HNMR (CDCl$_3$, 400 MHz): δ 7.65 (d, J=2.4 Hz, 1H), 7.36 (dd, J=8.8, 2.4 Hz, 1H), 6.96 (d, J=8.8 Hz, 1H), 3.95 (s, 3H), 3.87 (s, 3H), 2.52 (s, 3H), 2.18 (s, 3H).

Step 5: Methyl 5-(6-methoxy-4'-sulfamoyl-[1,1'-biphenyl]-3-yl)-3,4-dimethylthiophene-2-carboxylate (9e)

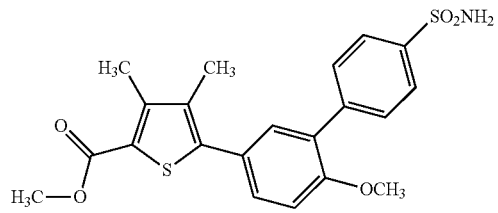 [SMILES: COC(=O)c1sc(-c2ccc(OC)c(-c3ccc(S(N)(=O)=O)cc3)c2)c(C)c1C]

4-aminosulfonylbenzene boronic acid (0.54 g, 2.68 mmol) and potassium carbonate (0.67 g, 4.86 mmol) were added to the solution of methyl 5-(3-bromo-4-methoxyphenyl)-3,4-dimethylthiophene-2-carboxylate (step-4, 0.9 g, 2.43 mmol) in a mixture of toluene:ethanol (5:20 ml) in a tube at 25° C. Nitrogen gas was bubbled through reaction mixture for 15 minutes. Tetrakis(triphenylphosphine)(0) palladium (0.14 g, 0.12 mmol) was added to the reaction mixture under nitrogen atmosphere and tube was sealed. The reaction mixture was heated at 95-100° C. for 1 hr under stirring. The progress of the reaction was monitored by TLC. The reaction mixture was cooled to 25° C. and filtered through celite. The celite cake was washed with ethyl acetate (30 ml). The combined filtrate was concentrated under reduced pressure to obtain a crude product. The crude product so obtained was purified by column chromatography using 40% ethyl acetate in hexanes as an eluent to obtain the title compound 9e (0.23 g, 21.2%).

MS: m/z 432 (M+1).

Step 6: 5-(6-methoxy-4'-sulfamoyl-[1,1'-biphenyl]-3-yl)-3,4-dimethylthiophene-2-carboxylic acid (9f)

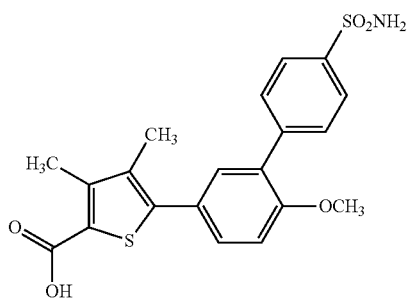 [SMILES: COc1ccc(-c2sc(C(=O)O)c(C)c2C)cc1-c1ccc(S(N)(=O)=O)cc1]

Methyl 5-(6-methoxy-4'-sulfamoyl-[1,1'-biphenyl]-3-yl)-3,4-dimethylthiophene-2-carboxylate (step-5, 0.2 g, 0.45 mmol) was suspended in ethanol (10 ml). Aqueous solution of NaOH (0.09 g. 2.24 mmol in water 2 ml) was added to the reaction mixture at 0° C. The reaction mixture was heated at 80° C. under stirring for 1.5 hour. The progress of the reaction was monitored by TLC. The reaction mixture was then concentrated under reduced pressure. Dilute hydrochloric acid was added to the separated aqueous layer to bring the pH of the solution to between 6 and 7. The resulting mixture was extracted with ethyl acetate (2×25 ml). The combined organic layer was dried over anhydrous $Na_2SO_4$. The solvent was evaporated from the dried organic layer under reduced pressure to obtain the title compound 9f (0.17 g, 86.0%).

MS: m/z 418 (M+1).

$^1$HNMR (DMSO-$d_6$, 400 MHz): δ 12.70 (bs-exchanges with $D_2O$, 1H), 7.75 (d, J=8.0 Hz, 2H), 7.67 (d, J=8.0 Hz, 2H), 7.50-7.62 (m, 4H), 7.26 (d, J=8.8 Hz, 1H), 3.83 (s, 3H), 2.45 (s, 3H), 2.17 (s, 3H).

Step 7: 5-(4'-(N-((dimethylamino)methylene)sulfamoyl)-6-methoxy-[1,1'-biphenyl]-3-yl)-N-methoxy-N,3,4-trimethylthiophene-2-carboxamide (9g)

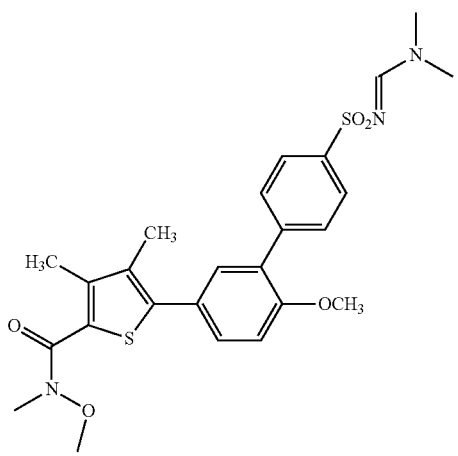

Oxalyl chloride (0.09 g, 0.06 ml, 0.72 mmol) was added drop wise to a solution of 5-(6-methoxy-4'-sulfamoyl-[1,1'-biphenyl]-3-yl)-3,4-dimethylthiophene-2-carboxylic acid (9f, 0.16 g, 0.36 mmol) in dichloromethane (10 ml) and DMF (0.05 g, 0.06 ml, 0.72 mmol) at 0° C. The reaction mixture was allowed to come to room temperature and stirred for 1.5 hr under nitrogen atmosphere. The progress of the reaction was monitored by TLC. The reaction mixture was then concentrated under reduced pressure. The residue so obtained was dissolved in dry dichloromethane (10 ml) and to this was added triethylamine (0.18 g, 0.25 ml, 1.79 mmol) followed by the addition of N,O-dimethylhydroxylamine hydrochloride (0.07 g, 0.72 mmol) under stirring. The reaction mixture was then stirred at room temperature for 2 hours. The progress of the reaction was monitored by TLC. Dichloromethane (10 mL) was added to the reaction mixture. The resultant mixture was washed with water (2×10 ml). The separated organic layer was dried over anhydrous sodium sulphate and concentrated at reduced pressure to get a crude product. The crude product so obtained was purified by column chromatography using 30% ethyl acetate in hexane as an eluent to obtain the title compound 9g (0.12 g, 65%).

MS: m/z 516 (M+1).

$^1$HNMR (CDCl$_3$, 400 MHz): δ 8.18 (s, 1H), 7.75 (d, J=8.0 Hz, 2H), 7.66 (d, J=8.4 Hz, 2H), 7.44 (dd, J=8.4, 2.4 Hz, 1H), 7.38 (d, J=2.4 Hz, 1H), 7.05 (d, J=8.4 Hz, 1H), 3.86 (s, 3H), 3.71 (s, 3H), 3.41 (s, 3H), 3.15 (s, 3H), 3.04 (s, 3H), 2.47 (s, 3H), 2.19 (s, 3H).

Step 8: 5'-(3,4-dimethyl-5-propionylthiophen-2-yl)-2'-methoxy-[1,1'-biphenyl]-4-sulfonamide (Compound 9)

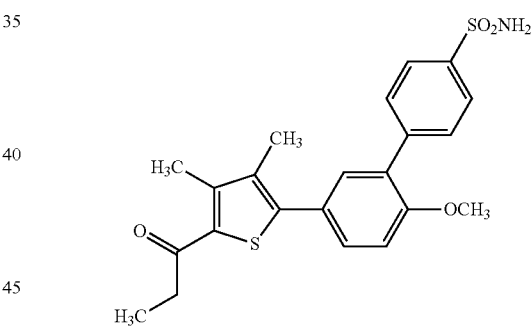

Ethyl magnesium bromide (0.14 g, 1.1 ml, 1.06 mmol) was added drop wise to a solution of 5-(4'-(N-((dimethylamino)methylene)sulfamoyl)-6-methoxy-[1,1'-biphenyl]-3-yl)-N-methoxy-N,3,4-trimethylthiophene-2-carboxamide (Step 7, 0.11 g, 0.21 mmol) in anhydrous THF (10 ml) at 25° C. under stirring. The reaction mixture was then heated to 70-75° C. for 1 hour. The progress of the reaction was monitored by TLC. The reaction mixture was then cooled to 0° C. The cooled reaction mixture was then quenched with a saturated solution of ammonium chloride (10 ml). The resultant mixture was then extracted with ethyl acetate (3×20 ml). The combined organic layer was dried over anhydrous $Na_2SO_4$. The solvent was evaporated from the organic layer under reduced pressure to obtain a crude product, which was then purified by column chromatography using 35% ethyl acetate in hexane as an eluent to obtain the title compound 9 (0.03 g, 33.0%).

MS: m/z 430 (M+1).

$^1$HNMR (CDCl$_3$, 400 MHz): δ 7.97 (d, J=8.0 Hz, 2H), 7.70 (d, J=8.0 Hz, 2H), 7.39-7.47 (m, 2H), 7.07 (d, J=8.4 Hz, 1H), 4.90 (bs-exchanges with D$_2$O, 2H), 3.87 (s, 3H), 2.86 (q, J=7.2 Hz, 2H), 2.53 (s, 3H), 2.20 (s, 3H), 1.21 (t, J=7.2 Hz, 3H).

EXAMPLE 5

Preparation of 5'-(1,3-dimethyl-5-propionyl-1H-pyrrol-2-yl)-2'-methoxy-[1,1'-biphenyl]-4-sulfonamide (Compound 10)

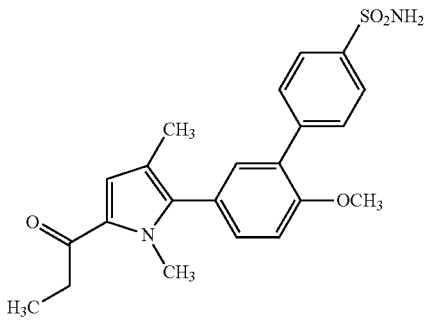 [SMILES: CCC(=O)c1cc(C)c(-c2ccc(OC)c(-c3ccc(S(N)(=O)=O)cc3)c2)n1C]

Step 1: Methyl 5-(3-bromo-4-methoxyphenyl)-1,4-dimethyl-1H-pyrrole-2-carboxylate (10a)

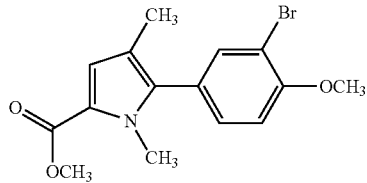 [SMILES: COC(=O)c1cc(C)c(-c2ccc(OC)c(Br)c2)n1C]

A solution of methyl 5-(3-bromo-4-methoxyphenyl)-4-methyl-1H-pyrrole-2-carboxylate (prepared according to the procedure reported in J. Org. Chem., 2009, 74(2), 903-905, Org. Lett., 2007, Vol. 9, 25, 5191-5194, 1.40 g, 4.32 mmol) in DMF (3 ml) was added to a solution of sodium hydride (0.21 g 60% in paraffin oil, 4.75 mmol) in DMF (2 ml) at 0° C. under stirring. Methyl iodide (0.67 g, 0.29 ml, 4.75 mmol) was then added to the reaction mixture. The reaction mixture was stirred at room temperature for 45 minutes. The progress of the reaction was monitored by TLC. The reaction mixture was quenched with water (5 ml) and then extracted with ethyl acetate (2×50 ml). The combined organic layer was dried over anhydrous Na$_2$SO$_4$. The solvent was evaporated from the dried organic layer under reduced pressure to obtain a crude product. The crude product was further purified by flash column chromatography using 20% ethyl acetate in hexanes as an eluent to obtain the title compound 10a (1.25 g, 85%).

MS: m/z 338 (M+1).

$^1$HNMR (CDCl$_3$, 400 MHz): δ 7.49 (d, J=2.0 Hz, 1H), 7.21 (dd, J=8.4, 2.0 Hz, 1H), 6.99 (d, J=2.0 Hz, 1H), 6.85 (s, 1H), 3.93 (s, 3H), 3.81 (s, 3H), 3.74 (s, 3H), 1.94 (s, 3H).

Step 2: Methyl 5-(6-methoxy-4'-sulfamoyl-[1,1'-biphenyl]-3-yl)-1,4-dimethyl-1H-pyrrole-2-carboxylate (10b)

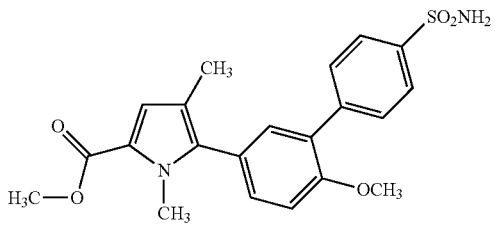 [SMILES: COC(=O)c1cc(C)c(-c2ccc(OC)c(-c3ccc(S(N)(=O)=O)cc3)c2)n1C]

4-aminosulfonylbenzene boronic acid (0.72 g, 3.57 mmol) and potassium carbonate (0.89 g, 6.50 mmol) were added to a solution of methyl 5-(3-bromo-4-methoxyphenyl)-1,4-dimethyl-1H-pyrrole-2-carboxylate (10a, 1.1 g, 3.25 mmol) in a mixture of toluene:ethanol (5:15 ml) in a tube at 25° C. Nitrogen gas was bubbled through the reaction mixture for 15 minutes. Tetrakis(triphenylphosphine)(0) palladium (0.18 g, 0.16 mmol) was then added to the reaction mixture under nitrogen atmosphere and the tube was sealed. The reaction mixture was heated at 95-100° C. for 1 hr under stirring. The progress of the reaction was monitored by TLC. The reaction mixture was then cooled to 25° C. and filtered through celite. The celite cake was washed with 10% methanol in DCM (30 ml). The combined filtrate was concentrated under reduced pressure to obtain a crude product, which was then purified by column chromatography using 40% ethyl acetate in hexanes as an eluent to obtain the title compound 10b (0.84 g, 62.6%).

MS: m/z 415 (M+1).

$^1$HNMR (CDCl$_3$, 400 MHz): δ 7.97 (d, J=8.4 Hz, 2H), 7.70 (d, J=8.4 Hz, 2H), 7.30 (dd, J=8.4, 2.4 Hz, 1H), 7.23 (d, J=2.4 Hz, 1H), 7.10 (d, J=8.4 Hz, 1H), 6.87 (s, 1H), 4.89 (bs-exchanges with D$_2$O, 2H), 3.88 (s, 3H), 3.81 (s, 3H), 3.76 (s, 3H), 2.01 (s, 3H).

Step 3: 5-(6-methoxy-4'-sulfamoyl-[1,1'-biphenyl]-3-yl)-1,4-dimethyl-1H-pyrrole-2-carboxylic acid 10c

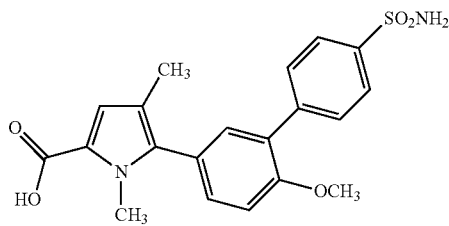 [SMILES: COc1ccc(-c2c(C)cc(C(=O)O)n2C)cc1-c1ccc(S(N)(=O)=O)cc1]

Methyl 5-(6-methoxy-4'-sulfamoyl-[1,1'-biphenyl]-3-yl)-1,4-dimethyl-1H-pyrrole-2-carboxylate (step-2, 0.77 g, 1.85 mmol) was suspended in ethanol (15 ml), to this was then added aqueous solution of NaOH (0.37 g. 9.29 mmol in 5 ml water) at 0° C. The reaction mixture was stirred at 25° C. for 15 hours. The progress of the reaction was monitored by TLC. The reaction mixture was concentrated under reduced pressure. The residue obtained after concentration was then dissolved in water (10 ml) and dilute hydrochloric acid was added to the mixture so obtained to bring the pH of the mixture to between 6 and 7. The mixture was then extracted with ethyl acetate (2×50 ml). The separated combined organic layer was then dried over anhydrous sodium sulfate. The solvent was evaporated from the dried organic layer under reduced pressure to obtain the title compound 10c (0.71 g, 95.9%).

MS: m/z 401 (M+1).

$^1$HNMR (DMSO-d$_6$, 400 MHz): δ 12.05 (bs-exchanges with D$_2$O, 1H), 7.85 (d, J=8.4 Hz, 2H), 7.71 (d, J=8.4 Hz, 2H), 7.38-7.41 (m, 3H), 7.26-7.30 (m, 2H), 6.76 (s, 1H), 3.85 (s, 3H), 3.70 (s, 3H), 1.96 (s, 3H).

Step 4: N-methoxy-5-(6-methoxy-4'-sulfamoyl-[1,1'-biphenyl]-3-yl)-N,1,4-trimethyl-1H-pyrrole-2-carboxamide (10d)

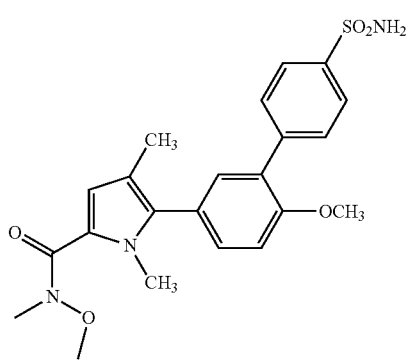 [SMILES: COc1ccc(-c2c(C)cc(C(=O)N(C)OC)n2C)cc1-c1ccc(S(N)(=O)=O)cc1]

HOBT (0.29 g, 1.92 mmol) was added to a solution of 5-(6-methoxy-4'-sulfamoyl-[1,1'-biphenyl]-3-yl)-1,4-dimethyl-1H-pyrrole-2-carboxylic acid (10c, 0.70 g, 1.75 mmol) in DMF (15 ml) under stirring at room temperature. N,O-dimethylhydroxylamine hydrochloride (0.33 g, 3.5 mmol) was then added to the reaction mixture. The reaction mixture was cooled to 0° C. and EDC (0.50 g, 2.60 mmol) and triethylamine (0.70 g, 0.97 ml, 7.00 mmol) were added to it. The reaction mixture was stirred at room temperature for 15 hours. The progress of the reaction was monitored by TLC. The reaction mixture was concentrated under reduced pressure. The residue obtained after concentration was mixed with ethyl acetate (50 ml) and the resultant mixture was washed with saturated sodium bicarbonate solution (10 ml) followed by washing with brine (10 ml). The organic layer separated was dried over anhydrous sodium sulphate and concentrated under reduced pressure to obtain a crude product. The crude product was further purified by flash column chromatography using 4% methanol in DCM as an eluent to obtain the title compound 10d (0.67 g, 87%).

MS: m/z 444 (M+1).

$^1$HNMR (CDCl$_3$, 400 MHz): δ 7.96 (d, J=8.4 Hz, 2H), 7.69 (d, J=8.4 Hz, 2H), 7.32 (dd, J=8.4, 2.0 Hz, 1H), 7.27 (d, J=2.4 Hz, 1H), 7.08 (d, J=8.4 Hz, 1H), 6.79 (s, 1H), 5.13 (bs-exchanges with D$_2$O, 2H), 3.87 (s, 3H), 3.74 (s, 3H), 3.70 (s, 3H), 3.35 (s, 3H), 2.03 (s, 3H).

Step 5: 5-(4'-(N-((dimethylamino)methylene)sulfamoyl)-6-methoxy-[1,1'-biphenyl]-3-yl)-N-methoxy-N,1,4-trimethyl-1H-pyrrole-2-carboxamide (10e)

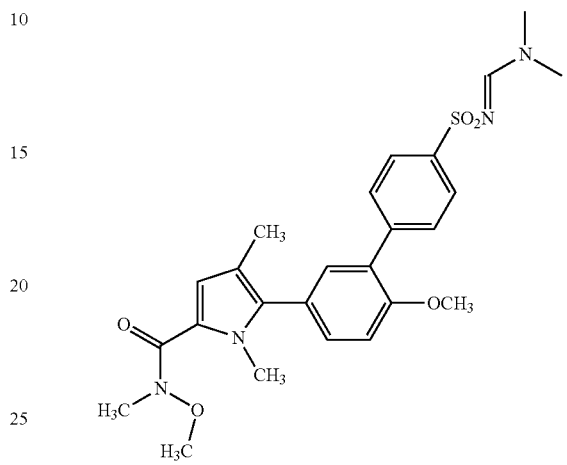

DMF (0.65 ml) and DMF acetal (0.19 g, 0.21 ml, 1.61 mmol) were added to a solution of N-methoxy-5-(6-methoxy-4'-sulfamoyl-[1,1'-biphenyl]-3-yl)-N,1,4-trimethyl-1H-pyrrole-2-carboxamide (10d, 0.65 g, 1.46 mmol) in ethyl acetate (13 ml) under stirring at room temperature. The mixture was stirred at room temperature for 15 hr under nitrogen atmosphere. The progress of the reaction was monitored by TLC. The reaction mixture was diluted with ethyl acetate (50 ml) and the mixture so obtained was washed with water (2×20 ml). The organic layer separated was dried over Na$_2$SO$_4$ and concentrated to obtain a crude product. The crude product was purified by flash column chromatography using 4% methanol in DCM as an eluent to obtain the title compound 10e (0.62 g, 84.9%).

MS: m/z 499 (M+1).

$^1$HNMR (CDCl$_3$, 400 MHz): δ 8.16 (s, 1H), 7.92 (d, J=8.4 Hz, 2H), 7.64 (d, J=8.4 Hz, 2H), 7.30 (dd, J=8.4, 2.0 Hz, 1H), 7.25 (d, J=2.0 Hz, 1H), 7.06 (d, J=8.4 Hz, 1H), 6.78 (s, 1H), 3.87 (s, 3H), 3.73 (s, 3H), 3.70 (s, 3H), 3.34 (s, 3H), 3.14 (s, 3H), 3.04 (s, 3H), 2.03 (s, 3H).

Step 6: 5'-(1,3-dimethyl-5-propionyl-1H-pyrrol-2-yl)-2'-methoxy-[1,1'-biphenyl]-4-sulfonamide (Compound 10)

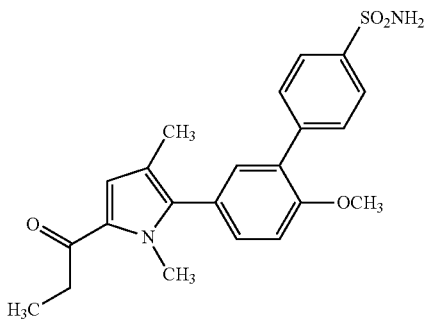 [SMILES: CCC(=O)c1cc(C)c(-c2ccc(OC)c(-c3ccc(S(N)(=O)=O)cc3)c2)n1C]

Ethyl magnesium bromide (0.53 g, 3.96 ml, 3.98 mmol) was added drop wise to a solution of 5-(4'-(N-((dimethylamino)methylene)sulfamoyl)-6-methoxy-[1,1'-biphenyl]-3-yl)-N-methoxy-N,1,4-trimethyl-1H-pyrrole-2-carboxamide (Step 5, 0.4 g, 0.80 mmol) in anhydrous THF (10 ml) under stirring at 25° C. The reaction mixture was heated at 70-75° C. for 1 hour. The progress of the reaction was monitored by TLC. The reaction mixture was then cooled to 0° C. and was quenched by addition of saturated solution of ammonium chloride (10 ml). The resulting mixture was extracted with ethyl acetate (3×30 ml). The combined organic layer was dried over anhydrous $Na_2SO_4$. The solvent was evaporated from the dried organic layer under reduced pressure to obtain a crude product, which was then purified by column chromatography using mixture of ethyl acetate and hexane as an eluent to obtain the title compound 10 (0.04 g, 12.12%).

MS: m/z 413 (M+1).

$^1$HNMR (CDCl$_3$, 400 MHz): δ 7.98 (d, J=8.4 Hz, 2H), 7.71 (d, J=8.4 Hz, 2H), 7.32 (dd, J=8.4, 2.4 Hz, 1H), 7.25 (d, J=2.4 Hz, 1H), 7.11 (d, J=8.4 Hz, 1H), 6.91 (s, 1H), 4.87 (bs-exchanges with D$_2$O, 2H), 3.90 (s, 3H), 3.80 (s, 3H), 2.83 (q, J=7.2 Hz, 2H), 2.05 (s, 3H), 1.23 (t, J=7.2 Hz, 3H).

EXAMPLE 19

Pharmacological Screening

Compounds were tested in a cell-based real-time kinetic assay in human IMR-32 cells with native expression of α7nAChR. The increase in intracellular Ca$^{2+}$ levels was measured in a Fluorometric Imaging Plate Reader (FLIPR). Test compound and agonist solutions were made in assay buffer (HBSS, pH 7.4, 20 mM HEPES, and 10 mM CaCl$_2$). Briefly, cells were plated into Poly-D-Lysine coated back-walled clear-bottom 96-well microplates at a density of 80,000 to 100,000 cells/well and incubated at 37° C./5% CO$_2$ for 40-48 h prior to the experiment. For evaluation of compound mediated potentiation of agonist response, growth media was removed from the wells and 200 μl of FLIPR calcium 4 dye (Molecular Devices), reconstituted in assay buffer, and was added to the wells. After dye loading, microplates were incubated for 30 mM at 37° C. and 30 mM at room temperature and then directly transferred to the FLIPR. Baseline fluorescence was monitored for the first 10 to 30 s followed by the addition of 25 μl of test compound solution and subsequent monitoring of fluorescence changes for up to 10 min. This was followed by addition of 25 μl of agonist solution (PNU-282987, 10 μM) and measurement of fluorescence for 4 mM. (Faghih R. et al. 2009, J. Med. Chem., 52, 3377-84.)

The compound induced fold increase in agonist response (fold PAM activity) was computed by dividing the maximum effect (Max-MM fluorescence) obtained with test compound in presence of agonist with the agonist-alone effect. EC$_{50}$ of the compound was calculated using GraphPad Prism software version 5.0, by plotting compound concentrations against fold PAM activity.

Fold activity at 1 μM concentration: Compounds of invention showed increase in the activity up to 30 folds compared to control.

The invention claimed is:

1. A compound of formula (I), its tautomeric forms, its stereoisomers, its sulfoxides, its N-oxides, its pharmaceutically acceptable salts, its polymorphs, its solvates, or its optical isomers

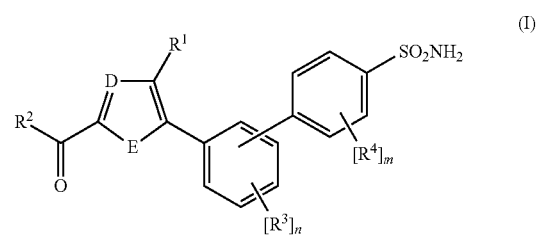

wherein,

'D' is selected from N and CR$^5$;

'E' is selected from S and NR$^6$;

with a proviso that when 'E' is NR$^6$, 'D' is not selected as N;

R$^1$ is selected from hydrogen or substituted- or unsubstituted- alkyl, substituted- or unsubstituted- alkenyl, halogen, perhaloalkyl, substituted- or unsubstituted- cycloalkyl, substituted- or unsubstituted- heterocyclyl, cyano, nitro, (R$^7$)(R$^8$)N—, R$^{7c}$C(=O)N(R$^8$)—, (R$^{7a}$)(R$^8$)NC(=A$^1$)N(R$^9$)—, R$^{7b}$OC(=O)NR$^{8a}$—, R$^{7b}$SO$_2$N(R$^{8a}$)—, R$^7$A$^1$, (R$^{7a}$)(R$^8$)NC(=O)—, and R$^{7b}$S(O)$_p$—, wherein 'p' is an integer ranging from 1 to 2;

R$^2$ is selected from substituted- or unsubstituted- alkyl, substituted- or unsubstituted- alkenyl, substituted- or unsubstituted- cycloalkyl, substituted- or unsubstituted- heterocyclyl, (R$^7$)(R$^8$)N—, (R$^7$)N(OR$^{7c}$)—, and R$^7$A$^1$—;

R$^3$ is selected independently at each occurrence from halogen, cyano, substituted- or unsubstituted- alkyl, substituted- or unsubstituted- cycloalkyl, substituted- or unsubstituted- heterocyclyl, (R$^{7a}$)(R$^{8a}$)NC(=O)—, R$^{7a}$A$^1$—, (R$^{7b}$)C(=O)N(R$^{8a}$)—, (R$^{7a}$)(R$^{8a}$)N—, (R$^{7a}$)(R$^{8a}$)NC(=A$^1$)N(R$^9$)—, (R$^{7a}$)(R$^{8a}$)NC(=O)O—, R$^{7b}$OC(=O)N(R$^{8a}$)—, R$^{7b}$S(O)$_p$—, wherein 'p' is an integer ranging from 1 to 2, and two R$^3$s and the carbon atoms to which they are attached can combine to form an substituted- or unsubstituted- 5 to 8 member cyclic system which may contain 1 to 3 heteroatoms/groups selected from —NH—, —S—, —O—, —C(=O)—, and —C(=S)—;

'n' is selected from 0, 1, 2 and 3;

R$^4$ is selected independently at each occurrence from halogen, cyano, substituted- or unsubstituted- alkyl, substituted- or unsubstituted- cycloalkyl, substituted- or unsubstituted- heterocyclyl, (R$^{7a}$)(R$^{8a}$)NC(=O)—, R$^{7a}$A$^1$—, (R$^{7b}$)C(=O)N(R$^{8a}$)—, (R$^{7a}$)(R$^{8a}$)N—, and two R$^4$s and the carbon atoms to which they are attached can combine to form a substituted- or unsubstituted- 5 to 8 membered cyclic system which may contain 1 to 3 heteroatoms/groups such as —NH—, —S—, —O—, —C(=O)—, and —C(=S)—;

'm' is selected from 0, 1, 2 and 3;

R$^5$ is selected from hydrogen, halogen, substituted- or unsubstituted- alkyl, substituted- or unsubstituted- aryl, substituted- or unsubstituted- heteroaryl, substituted- or unsubstituted- cycloalkyl, substituted- or unsubstituted- heterocyclyl, (R$^7$)(R$^8$)N—, and R$^{7c}$C(=O)—;

R$^6$ is selected from hydrogen, substituted- or unsubstituted- alkyl, substituted- or unsubstituted- cycloalkyl, and R$^{7c}$C(=O)—;

R$^7$ and R$^8$ are independently selected from hydrogen, substituted- or unsubstituted- alkyl, substituted- or unsubstituted- aryl, substituted- or unsubstituted- heteroaryl, substituted- or unsubstituted- cycloalkyl, and substituted- or unsubstituted- heterocyclyl;

$R^{7a}$, $R^{8a}$, and $R^9$ are independently selected from hydrogen, substituted- or unsubstituted- alkyl, and substituted- or unsubstituted- cycloalkyl;

$R^{7b}$ is selected from substituted- or unsubstituted- alkyl, and substituted- or unsubstituted- cycloalkyl;

$R^{7c}$ is selected from substituted- or unsubstituted- alkyl, substituted- or unsubstituted- aryl, substituted- or unsubstituted- heteroaryl, substituted- or unsubstituted- cycloalkyl, and substituted- or unsubstituted- heterocyclyl;

the substituents on 'alkyl' and 'alkenyl' are selected from the group consisting of oxo, halogen, nitro, cyano, perhaloalkyl, substituted or unsubstituted cycloalkyl, substituted or unsubstituted cycloalkenyl, substituted or unsubstituted aryl, substituted or unsubstituted heteroaryl, substituted or unsubstituted heterocyclyl, $R^{10b}A^1$—, $R^{10a}SO_2$—, $R^{10a}OC(=O)$—, $R^{10a}C(=O)O$—, $R^{10}N(H)C(=O)$—, $R^{10}N(alkyl)C(=O)$—, $R^{10a}C(=O)N(H)$—, $R^{10}N(H)$—, $R^{10}N(alkyl)$—, $R^{10}N(H)C(=A^1)N(H)$—, and $R^{10}N(alkyl)C(=A^1)N(H)$—;

the substituents on 'cycloalkyl' and 'cycloalkenyl' are selected from the group consisting of oxo, halogen, nitro, cyano, substituted or unsubstituted alkyl, substituted or unsubstituted alkenyl, perhaloalkyl, substituted or unsubstituted aryl, substituted or unsubstituted heteroaryl, substituted or unsubstituted heterocyclyl, $R^{10b}A^1$—, $R^{10a}SO_2$—, $R^{10a}C(=O)$—, $R^{10a}OC(=O)$—, $R^{10a}C(=O)O$—, $R^{10}(H)NC(=O)$—, $R^{10}N(alkyl)C(=O)$—, $R^{10a}C(=O)N(H)$—, $R^{10}(H)N$—, $R^{10}(alkyl)N$—, $R^{10}(H)NC(=A^1)N(H)$—, and $R^{10}(alkyl)NC(=A^1)N(H)$—;

the substituents on 'aryl' are selected from the group consisting of halogen, nitro, cyano, hydroxy, substituted or unsubstituted alkyl, substituted or unsubstituted alkenyl, perhaloalkyl, substituted or unsubstituted cycloalkyl, substituted or unsubstituted cycloalkenyl, substituted- or unsubstituted- heterocycle, alkyl-O—, perhaloalkyl-O—, alkyl(alkyl)N—, alkyl(H)N—, $H_2N$—, alkyl-$SO_2$—, perhaloalkyl-$SO_2$—, alkyl-C(=O)N(alkyl)—, alkyl-C(=O)N(H)—, alkyl(alkyl)NC(=O)—, alkyl(H)NC(=O)—, $H_2NC(=O)$—, alkyl(alkyl)$NSO_2$—, alkyl(H)$NSO_2$—, and $H_2NSO_2$—;

the substituents on 'heteroaryl' are selected from the group consisting of halogen, nitro, cyano, hydroxy, substituted- or unsubstituted- alkyl, substituted- or unsubstituted- alkenyl, perhaloalkyl, substituted- or unsubstituted- cycloalkyl, substituted- or unsubstituted- cycloalkenyl, substituted- or unsubstituted- heterocycle, alkyl-O—, perhaloalkyl-O—, alkyl(alkyl)N—, alkyl(H)N—, $H_2N$—, alkyl-$SO_2$—, perhaloalkyl-$SO_2$—, alkyl-C(=O)N(alkyl)—, alkyl-C(=O)N(H)—, alkyl(alkyl)NC(=O)—, alkyl(H)NC(=O)—, $H_2NC(=O)$—, alkyl(alkyl)$NSO_2$—, alkyl(H)$NSO_2$—, and $H_2NSO_2$—;

the substituents on ring carbon of 'heterocycle' is selected from the group consisting of halogen, nitro, cyano, oxo, substituted- or unsubstituted- alkyl, substituted- or unsubstituted- alkenyl, perhaloalkyl, substituted- or unsubstituted- cycloalkyl, substituted- or unsubstituted- cycloalkenyl, substituted- or unsubstituted- aryl, substituted- or unsubstituted- heteroaryl, substituted- or unsubstituted- heterocyclyl, substituted- or unsubstituted- alkyl, $R^{10b}A^1$—, —$R^{10a}OC(=O)$—, $R^{10}(H)NC(=O)$—, $R^{10}N(alkyl)C(=O)$—, $R^{10a}C(=O)N(H)$—, $R^{10}(H)N$—, $R^{10}(alkyl)N$—, $R^{10}(H)NC(=A^1)N(H)$—, and $R^{10}(alkyl)NC(=A^1)N(H)$—;

the substituents on ring nitrogen of 'heterocycle' is selected from the group consisting of substituted- or unsubstituted- alkyl, substituted- or unsubstituted- alkenyl, substituted- or unsubstituted- cycloalkyl, substituted- or unsubstituted- cycloalkenyl, substituted- or unsubstituted- aryl, substituted- or unsubstituted- heteroaryl, $R^{10a}SO_2$—, $R^{10a}C(=O)$—, $R^{10a}OC(=O)$—, $R^{10}(H)NC(=O)$—and $R^{10}N(alkyl)C(=O)$—;

the "5 to 8 membered cyclic system" is substituted with 1 to 3 substituents selected from the group consisting of halogen, nitro, cyano, aryl, heteroaryl, alkyl, alkenyl, alkynyl, $R^{10a}C(=O)$—, $R^{10a}SO_2$—, $R^{10b}A^1$—, $R^{10a}OC(=O)$—, $R^{10a}C(=O)O$—, $(R^{10})(H)NC(=O)$—, $(R^{10})(alkyl)NC(=O)$—, $R^{10a}C(=O)N(H)$—, $(R^{10})(H)N$—, $(R^{10})(alkyl)N$—, $(R^{10})(H)NC(=A^1)N(H)$—, and $(R^{10})(alkyl)NC(=A^1)N(H)$—;

$R^{10}$ is selected from the group consisting of hydrogen, alkyl, alkenyl, cycloalkyl, cycloalkenyl, aryl, heteroaryl, and heterocyclyl;

$R^{10a}$ is selected from the group consisting of alkyl, alkenyl, perhaloalkyl, cycloalkyl, cycloalkenyl, aryl, heteroaryl, and heterocyclyl;

$R^{10b}$ is selected from the group consisting of hydrogen, alkyl, alkenyl, perhaloalkyl, cycloalkyl, cycloalkenyl, aryl, heteroaryl, and heterocyclyl;

$A^1$ is selected from S and O.

2. The compound of formula I, its tautomeric forms, its stereoisomers, its sulfoxides, its N-oxides, its pharmaceutically acceptable salts, its polymorphs, its solvates, its optical isomers, as claimed in claim 1, wherein D is selected from the group consisting of —CH=, —C(alkyl)=, and —N=.

3. The compound of formula I, its tautomeric forms, its stereoisomers, its sulfoxides, its N-oxides, its pharmaceutically acceptable salts, its polymorphs, its solvates, its optical isomers, as claimed in claim 1, wherein E is selected from —S- and —N(alkyl)-.

4. The compound of formula I, its tautomeric forms, its stereoisomers, its sulfoxides, its N-oxides, its pharmaceutically acceptable salts, its polymorphs, its solvates, its optical isomers, as claimed in claim 1, wherein $R^I$ is selected as substituted- or unsubstituted- alkyl.

5. The compound of formula I, its tautomeric forms, its stereoisomers, its sulfoxides, its N-oxides, its pharmaceutically acceptable salts, its polymorphs, its solvates, its optical isomers, as claimed in claim 1, wherein $R^2$ is selected from substituted-or unsubstituted- alkyl and substituted- or unsubstituted- heterocyclyl.

6. The compound of formula I, its tautomeric forms, its stereoisomers, its sulfoxides, its N-oxides, its pharmaceutically acceptable salts, its polymorphs, its solvates, its optical isomers, as claimed in claim 1, wherein $R^3$ is selected from halogen, $R^{7a}A$—, and $(R^{7a})(R^{8a})N$—; and p is preferably selected from 0 and 1.

7. The compound of formula I, its tautomeric forms, its stereoisomers, its sulfoxides, its N-oxides, its pharmaceutically acceptable salts, its polymorphs, its solvates, its optical isomers, as claimed in claim 1, wherein m is selected as 0.

8. The compound of formula I, its tautomeric forms, its stereoisomers, its sulfoxides, its N-oxides, its pharmaceutically acceptable salts, its polymorphs, its solvates, its optical isomers, as claimed in claim 1, wherein D is selected from —CH=, —C(alkyl)=, and —N=;

E is selected from —S—and —N(alkyl-;

$R^I$ is selected as substituted- or unsubstituted- alkyl;

R² is selected from substituted- or unsubstituted- alkyl and substituted- or unsubstituted heterocyclyl;

R³ is selected from halogen, $R^{7a}A—$, and $(R^{7a})(R^{8a})N—$;

p is selected from 0 and 1; and m is selected as 0.

9. The compound of formula (I), its tautomeric forms, its stereoisomers, its sulfoxides, its N-oxides, its pharmaceutically acceptable salts, its polymorphs, its solvates, its optical isomers, as claimed in claim 1, wherein the compound is selected from—

- 2'-Methoxy-5'-(3-methyl-5-propionylthiophen-2-yl)-[1,1'-biphenyl]-4-sulfonamide;
- 2'-chloro-5'-(3-methyl-5-propionylthiophen-2-yl)-[1,1'-biphenyl]-4-sulfonamide;
- 3'-(3-methyl-5-propionylthiophen-2-yl)-[1,1'-biphenyl]-4-sulfonamide;
- 2'-(dimethylamino)-5'-(3-methyl-5-propionylthiophen-2-yl)-[1,1'-biphenyl]-4-sulfonamide;
- 2'-methoxy-5'-(4-methyl-2-(piperidine-1-carbonyl)thiazol-5-yl)—[1,1'-biphenyl]-4-sulfonamide;
- 2'-methoxy-5'-(4-methyl-2-(pyrrolidine-1-carbonyl)thiazol-5-yl)—[1,1'-biphenyl]-4-sulfonamide;
- 2'-chloro-5'-(4-methyl-2-(pyrrolidine-1-carbonyl)thiazol-5-yl)-[1,1'-biphenyl]-4-sulfonamide;
- 2'-methoxy-5'-(4-methyl-2-propionylthiazol-5-yl)-[1,1'-biphenyl]-4-sulfonamide;
- 5'-(3,4-dimethyl-5-propionylthiophen-2-yl)-2'-methoxy-[1,1'-biphenyl]-4-sulfonamide;
- 5'-(1,3-dimethyl-5-propionyl-1H-pyrrol-2-yl)-2'-methoxy-[1,1'-biphenyl]-4-sulfonamide (Compound 10).

10. A pharmaceutical composition comprising a compound of claim 1 and a pharmaceutically acceptable carrier.

* * * * *